(12) United States Patent
Hu et al.

(10) Patent No.: US 6,251,919 B1
(45) Date of Patent: Jun. 26, 2001

(54) HETEROCYCLIC SUBSTITUTED ANILINE CALCIUM CHANNEL BLOCKERS

(75) Inventors: Lain-Yen Hu; Michael Francis Rafferty; Todd Robert Ryder, all of Ann Arbor, MI (US)

(73) Assignee: Warner-Lambert, Morris Plains, NJ (US)

( * ) Notice: Subject to any disclaimer, the term of this patent is extended or adjusted under 35 U.S.C. 154(b) by 0 days.

(21) Appl. No.: 09/319,900
(22) PCT Filed: Nov. 20, 1998
(86) PCT No.: PCT/US98/25007
§ 371 Date: Jun. 14, 1999
§ 102(e) Date: Jun. 14, 1999
(87) PCT Pub. No.: WO99/43658
PCT Pub. Date: Sep. 2, 1999

Related U.S. Application Data
(60) Provisional application No. 60/076,141, filed on Feb. 27, 1998.

(51) Int. Cl.[7] ............... A61K 31/445; C07D 401/06
(52) U.S. Cl. .......... 514/318; 514/212; 514/326; 514/422; 514/426; 514/255; 540/596; 544/360; 546/194; 546/214; 546/244; 548/557
(58) Field of Search .................. 514/212, 318, 514/326, 422, 426, 255; 540/596, 605; 544/360; 546/194, 214, 244; 548/557

(56) References Cited

U.S. PATENT DOCUMENTS

| | | | |
|---|---|---|---|
| 3,381,012 | * 4/1968 | Zenitz et al. | 546/176 |
| 3,686,187 | * 8/1972 | Cole et al. | 546/223 |
| 3,691,176 | * 9/1972 | Hallas et al. | 546/223 |
| 5,232,929 | 8/1993 | Desai | 514/314 |
| 5,332,817 | 7/1994 | Desai et al. | 546/16 |
| 5,420,297 | 5/1995 | Matsuo et al. | 548/525 |
| 5,952,349 | * 9/1999 | Asberom et al. | 514/316 |

FOREIGN PATENT DOCUMENTS

| | | |
|---|---|---|
| 156433 | * 2/1985 | (EP) . |
| 47-020157 | * 3/1971 | (JP) . |
| 92/02501 | 2/1992 | (WO) . |
| 92/02502 | 2/1992 | (WO) . |
| 93/01170 | 1/1993 | (WO) . |
| 93/15052 | 8/1993 | (WO) . |
| 93/15073 | 8/1993 | (WO) . |
| 93/15080 | 8/1993 | (WO) . |
| 93/22302 | 11/1993 | (WO) . |
| 94/13291 | 6/1994 | (WO) . |
| 94/14786 | 7/1994 | (WO) . |
| 95/04027 | 2/1995 | (WO) . |
| 95/11238 | 4/1995 | (WO) . |
| 95/11240 | 4/1995 | (WO) . |
| 95/12612 | 5/1995 | (WO) . |
| 95/13817 | 5/1995 | (WO) . |
| 95/24390 | 9/1995 | (WO) . |
| 95/26327 | 10/1995 | (WO) . |
| 95/33722 | 12/1995 | (WO) . |
| 95/33723 | 12/1995 | (WO) . |
| 96/02494 | 2/1996 | (WO) . |
| 96/18628 | * 6/1996 | (WO) . |
| 96/21641 | 7/1996 | (WO) . |
| 97/10210 | 3/1997 | (WO) . |
| 97/23216 | 7/1997 | (WO) . |
| 97/26258 | * 7/1997 | (WO) . |
| 98/01425 | * 1/1998 | (WO) . |

OTHER PUBLICATIONS

Ohkubo "Roles of substance P and somatostatin on transmission of nociceptive . . . " CA108;180639, 1987.*

* cited by examiner

*Primary Examiner*—Ceila Chang
(74) *Attorney, Agent, or Firm*—Todd M. Crissey; Charles W. Ashbrook

(57) ABSTRACT

The present invention provides compounds that block calcium channels having the Formula I shown below.

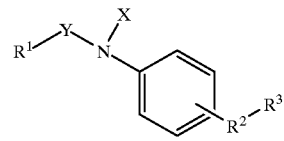

The present invention also provides methods of using the compounds of Formula I to treat stroke, cerebral ischemia, head trauma, epilepsy, asthma, amyotrophic lateral sclerosis, or pain and to pharmaceutical compositions that contain the compounds of Formula I.

17 Claims, No Drawings

HETEROCYCLIC SUBSTITUTED ANILINE CALCIUM CHANNEL BLOCKERS

This application is a 371 of PCT/US98/25007 filed Nov. 20, 1998 which claims priority benefit of Provisional Application No. 60/076,141 filed Feb. 27, 1998.

FIELD OF THE INVENTION

The present invention relates to compounds that act to block calcium channels; methods of using the compounds to treat stroke, cerebral ischemia, pain, head trauma, asthma, amyotrophic lateral sclerosis, or epilepsy; and to pharmaceutical compositions that contain the compounds of the present invention.

BACKGROUND OF THE INVENTION

The entry of excessive amounts of calcium ions into neurons following an ischemic episode or other neuronal trauma has been well documented. Uncontrolled high concentrations of calcium in neurons initiates a cascade of biochemical events that disrupts normal cellular processes. Among these events are the activation of proteases and lipases, breakdown of neuronal membranes and the formation of free radicals, which may ultimately lead to cell death. Several types of calcium channels have been discovered and called the L, N, P, Q, R, and T types. Each type possesses distinct structural features, functional properties and cellular/subcellular distributions. Type selective calcium channel blockers have been identified. For example, SNX-111 has been shown to be a selective N-type calcium channel blocker and has demonstrated activity in a number of models of ischemia and pain (Bowersox S. S., et al., *Drug News and Perspective*, 1994: 7:261–268 and references cited therein). The compounds of the present invention are calcium channel blockers that can block N-type calcium channels and can be used to treat stroke, pain, cerebral ischemia, head trauma, and epilepsy.

SUMMARY OF THE INVENTION

The present invention provides compounds having the Formula I

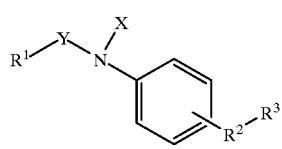

I wherein each n is independently 0 to 3;

R$^1$ is C$_1$–C$_8$ alkyl, substituted C$_1$–C$_8$ alkyl, C$_3$–C$_8$ cycloalkyl, substituted C$_3$–C$_8$ cycloalkyl, hetercycloalkyl, substituted hetercycloalkyl, C$_2$–C$_8$ alkenyl, C$_3$–C$_8$ cycloalkenyl, aryl, substituted aryl, heteroaryl, substituted heteroaryl, or arylalkyl;

Y is

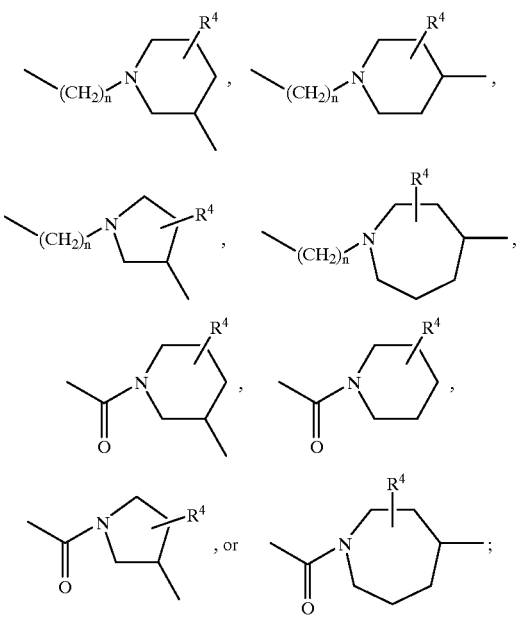

X is C$_1$–C$_8$ alkyl, C$_1$–C$_8$ substituted alkyl, C$_2$–C$_8$ alkenyl, substituted C$_2$–C$_8$ alkenyl, arylalkyl, substituted arylalkyl, heteroarylalkyl, substituted heteroarylalkyl, cycloalkylalkyl, or substituted cycloalkylalkyl;

R$^2$ is absent, —O—, (CH$_2$)$_n$-, O(CH$_2$)$_n$-, (CH$_2$)$_n$O—, N(R$^5$)(CH$_2$)$_n$-, (CH$_2$)$_n$N(R$^5$)- S(CH$_2$)$_n$-, (CH$_2$)$_n$S—, —C=C—, or —C≡C—;

R$^3$ is monocylic aryl, substituted monocyclic aryl, heteroaryl, substituted heteroaryl, heterocyclic, substituted heterocyclic, C$_1$–C$_8$ alkyl, substituted C$_1$–C$_8$ alkyl, C$_3$–C$_{10}$ cycloalkyl, substituted C$_3$–C$_{10}$ cycloalkyl;

R$^4$, R$^5$ are independently H or C$_1$–C$_8$ alkyl; and the pharmaceutically acceptable salts, esters, amides, and prodrugs thereof.

In a preferred embodiment of the compound of Formula I, R$^2$ is O(CH$_2$)$_n$-or -(CH$_2$)$_n$- and R$^3$ is phenyl.

In another preferred embodiment of the compounds of Formula I, X is C$_2$–C$_8$ alkenyl or C$_1$–C$_8$ alkyl and Y is

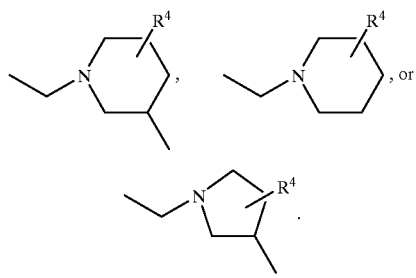

In another preferred embodiment of the compounds of Formula I, R$^4$ is hydrogen and R$^1$ is 3,3-dimethylbutyl.

In another preferred embodiment of the compounds of Formula I, R$^3$ is phenyl;

Y is

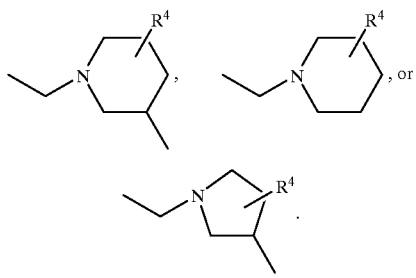

R⁴ is hydrogen;
X is 3-methyl-but-2 enyl; and
$R^1$ is $C_1$–$C_8$ alkyl, substituted $C_1$–$C_8$ alkyl, $C_3$–$C_8$ cycloalkyl, substituted $C_3$–$C_8$ cycloalkyl, hetercycloalkyl, substituted heteroalkyl, $C_2$–$C_8$ alkenyl, substituted $C_3$–$C_8$ cycloalkenyl, aryl, substituted aryl, heteroaryl, substituted heteroaryl, or arylalkyl.

In another preferred embodiment of the compounds of Formula I, Y is

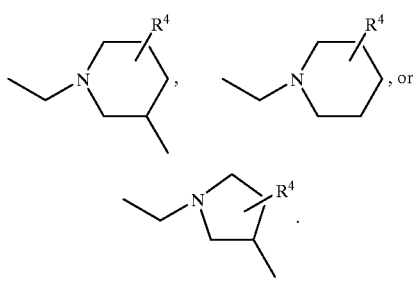

In another preferred embodiment of the compounds of Formula I, X is 3-methyl-but-2 enyl or 3-methylbutyl.

In another preferred embodiment of the compounds of Formula I, $R^1$ is $C_1$–$C_8$ alkyl, phenyl, pyrrolyl, piperazinyl, imidazolyl, pyridyl, or pyranyl.

In another preferred embodiment of the compounds of Formula I, $R^4$ is hydrogen.

In a most preferred embodiment of the present invention, the compounds are:

(4-Benzyloxy-phenyl)-(3-methyl-but-2-enyl)-[1-(3-methyl-butyl)-piperidin-4-yl]-amine;
(4-Benzyloxy-phenyl)-[1-(3,3-dimethyl-butyl)-piperidin-4-yl]-(3-methyl-but-2-enyl)-amine;
(4-Benzyloxy-phenyl)-[1-(4-tert-butyl-benzyl)-piperidin-4-yl]-(3-methyl-but-2-enyl)-amine;
(4-Benzyloxy-phenyl)-[1-(4-bromo-benzyl)-piperidin-4-yl]-(3-methyl-but-2-enyl)-amine;
4-{4[(4-Benzyloxy-phenyl)-(3-methyl-but-2-enyl)-amino]-piperidin-1-ylmethyl}-phenol;
(4-Benzyloxy-phenyl)-[1-(4-dimethylamino-benzyl)-piperidin-4-yl]-(3-methyl-but-2-enyl)-amine;
(4-Benzyloxy-phenyl)-(3-methyl-but-2-enyl)-[1 -(1H-pyrrol-2-ylmethyl)-piperidin-4-yl]-amine;
(4-Benzyloxy-phenyl)-[1-(1H-imidazol-4-ylmethyl)-piperidin-4-yl]-(3-methyl-but-2-enyl)-amine;
(4-Benzyloxy-phenyl)-(3-methyl-but-2-enyl)-(1-pyridin-2-ylmethyl-piperidin-4-yl)-amine;
(4-Benzyloxy-phenyl)-(3-methyl-but-2-enyl)-[1-(tetrahydro-pyran-4-yl)-piperidin-4-yl]-amine;
{4-[(4-Benzyloxy-phenyl)-(3-methyl-but-2-enyl)-amino]-piperidin-1-yl}-[1-(3-methyl-butyl)-piperidin-2-yl]-methanone;
{4-[(4-Benzyloxy-phenyl)-(3-methyl-but-2-enyl)-amino]-piperidin-1-yl }-[1-(3-methyl-butyl)-piperidin-3-yl]-methanone;
{4-[(4-Benzyloxy-phenyl)-(3-methyl-but-2-enyl)-amino]-piperidin-1-yl }-[1-(3-methyl-butyl)-piperidin-4-yl]-methanone;
{4-[(4-Benzyloxy-phenyl)-(3-methyl-but-2-enyl)-amino]-piperidin-1-yl}-[4-methyl-1-(3-methyl-butyl)-piperazin-2-yl]-methanone;
{4-[(4-Benzyloxy-phenyl)-(3-methyl-but-2-enyl)-amino]-piperidin-1-yl}-[4-isopropyl-1-(3-methyl-butyl)-piperazin-2-yl]-methanone;
{4-[(4-Benzyloxy-phenyl)-(3-methyl-but-2-enyl)-amino]-piperidin-1-yl}-[6-methyl-1-(3-methyl-butyl)-piperidin-2-yl]-methanone;
{4-[(4-Benzyloxy-phenyl)-(3-methyl-but-2-enyl)-amino]-piperidin-1-yl}-[4-methyl-1-(3-methyl-butyl)-piperidin-2-yl]-methanone;
{4-[(4-Benzyloxy-phenyl)-(3-methyl-but-2-enyl)-amino]-piperidin-1-yl}-[3-methyl-1-(3-methyl-butyl)-piperidin-2-yl]-methanone;
(4-Benzyloxy-phenyl)-[1-(4-tert-butyl-benzyl)-piperidin-4-yl]-(3-methyl-butyl)-amine;
4-Benzyloxy-phenyl)-[1-(4-dimethylamino-benzyl)-piperidin-4-yl]-(3-methyl-butyl)-amine;
(4-Benzyloxy-phenyl)-[1-(4-methoxy-benzyl)-piperidin4-yl]-(3-methyl-butyl)-amine;
(4-Benzyloxy-phenyl)-[1-(4-ethoxy-benzyl)-piperidin-4-yl]-(3-methyl-butyl)-amine;
(4-Benzyloxy-phenyl)-(3-methyl-butyl)-[1-(1H-pyrrol-2-ylmethyl)-piperidin-4-yl]-amine;
(4-Benzyloxy-phenyl)-(3-methyl-butyl)-[1-(4-methylsulfanyl-benzyl)-piperidin-4-yl]-amine;
(4-Benzyloxy-phenyl)-[1-(4-methanesulfinyl-benzyl)-piperidin-4-yl]-(3-methyl-butyl)-amine;
(4-Benzyloxy-phenyl)-[1-(4-isopropoxy-benzyl)-piperidin-4-yl]-(3-methyl-butyl)-amine;
(4-Benzyloxy-phenyl)-[1-(4-tert-butyl-benzyl)-piperidin-3-yl]-(3-methyl-butyl)-amine;
(4-Benzyloxy-phenyl)-[1-(4-dimethylamino-benzyl)-piperidin-3-yl]-(3-methyl-butyl)-amine;
(4-Benzyloxy-phenyl)-[1-(4methoxy-benzyl)-piperidin-3-yl]-(3-methyl-butyl)-amine;
(4-Benzyloxy-phenyl)-[1-(4-ethoxy-benzyl)-piperidin-3-yl]-(3-methyl-butyl)-amine;
(4-Benzyloxy-phenyl)-[(3-methyl-butyl)-[1-(1H-pyrrol-2-ylmethyl)-piperidin-3-yl]-amine;
(4-Benzyloxy-phenyl)-(3-methyl-butyl)-[1-(4-methylsulfanyl-benzyl)-piperidin-3-yl]-amine;
(4-Benzyloxy-phenyl)-[1-(4-methanesulfinyl-benzyl)-piperidin-3-yl]-(3-methyl-butyl)-amine;
(4-Benzyloxy-phenyl)-[1-(4-isopropoxy-benzyl)-piperidin-3-yl]-(3-methyl-butyl)-amine;
(4-Benzyloxy-phenyl)-[1-(4-tert-butyl-benzyl)-piperidin-3-yl]-(3-methyl-but-2-enyl)-amine;
(4-Benzyloxy-phenyl)-[1-(4-dimethylamino-benzyl)-piperidin-3-yl]-(3-methyl-but-2-enyl)-amine;
(4-Benzyloxy-phenyl)-[1-(4-methoxy-benzyl)-piperidin-3-yl]-(3-methyl-but-2-enyl)-amine;

(4-Benzyloxy-phenyl)-[1-(4-ethoxy-benzyl)-piperidin-3-yl]-(3-methyl-but-2-enyl)-amine;
(4-Benzyloxy-phenyl)-(3-methyl-butyl)-[1-(1H-pyrrol-2-ylmethyl)-piperidin-3-yl]-amine;
(4-Benzyloxy-phenyl)-(3-methyl-but-2-enyl)-[1-(4-methylsulfanyl-benzyl)-piperidin-3-yl]-amine;
(4-Benzyloxy-phenyl)-[1-(4-methanesulfinyl-benzyl)-piperidin-3-yl]-(3-methyl-but-2-enyl)-amine;
(4-Benzyloxy-phenyl)-[1-(4-isopropoxy-benzyl)-piperidin-3-yl]-(3-methyl-but-2-enyl)-amine;
(4-Benzyloxy-phenyl)-[1-(4-tert-butyl-benzyl)-pyrrolidin-3-yl]-(3-methyl-butyl)-amine;
(4-Benzyloxy-phenyl)-[1-(4-dimethylamino-benzyl)-pyrrolidin-3-yl]-(3-methyl-butyl)-amine;
(4-Benzyloxy-phenyl)-[1-(4-methoxy-benzyl)-pyrrolidin-3-yl]-(3-methyl-butyl)-amine;
(4-Benzyloxy-phenyl)-[1-(4-ethoxy-benzyl)-pyrrolidin-3-yl]-(3-methyl-butyl)-amine;
(4-Benzyloxy-phenyl)-(3-methyl-butyl)-[1-(1H-pyrrol-2-ylmethyl)-pyrrolidin-3-yl]-amine;
(4-Benzyloxy-phenyl)-(3-methyl-butyl)-[1-(4-methylsulfanyl-benzyl)-pyrrolidin-3-yl]-amine;
(4-Benzyloxy-phenyl)-[1-(4-methanesulfinyl-benzyl)-pyrrolidin-3-yl]-(3-methyl-butyl)-amine;
(4-Benzyloxy-phenyl-[1-(4-isopropoxy-benzyl)-pyrrolidin-3-yl]-(3-methyl-butyl)-amine;
(1-Benzo[1,3]dioxol-5-ylmethyl-piperidin-4-yl)-(4-benzyloxy-phenyl)-(3-methyl-butyl)-amine;
(4-Benzyloxy-phenyl)-[1-(4-bromo-benzyl)-piperidin-4-yl]-(3-methyl-butyl)-amine;
(4-Benzyloxy-phenyl)-[1-(4chloro-benzyl)-piperidin-4-yl]-(3-methyl-butyl)-amine;
(1-Benzo[1,3]dioxol-5-ylmethyl-piperidin-3-yl)-(4-benzyloxy-phenyl)-(3-methyl-butyl)-amine;
(4-Benzyloxy-phenyl)-[1-(4-bromo-benzyl)-piperidin-3-yl]-(3-methyl-butyl)-amine;
(4-Benzyloxy-phenyl)-[1-(4chloro-benzyl)-piperidin-3-yl]-(3-methyl-butyl)-amine;
(1-Benzo[1,3]dioxol-5-ylmethyl-piperidin-3-yl)-(4-benzyloxy-phenyl)-(3-methyl-but-2-enyl)-amine;
(4-Benzyloxy-phenyl)-[1-(4-bromo-benzyl)-piperidin-3-yl]-(3-methyl-but-2-enyl)-amine;
(4-Benzyloxy-phenyl)-[1-(4-chloro-benzyl)-piperidin-3-yl]-(3-methyl-but-2-enyl)-amine;
(1-Benzo[1,3]dioxol-5-ylmethyl-pyrrolidin-3-yl)-(4-benzyloxy-phenyl)-(3-methyl-but-2-enyl)-amine;
(4-Benzyloxy-phenyl)-[1-(4-bromo-benzyl)-pyrrolidin-3-yl]-(3-methyl-but-2-enyl)-amine;
(4Benzyloxy-phenyl)-[1-(4-chloro-benzyl)-pyrrolidin-3-yl]-(3-methyl-but-2-enyl)-amine;
N-Benzyl-N'-[1-(4-tert-butyl-benzyl)-piperidin-4-yl]-N'-(3-methyl-but-2-enyl)buzene-1,4-diamine;
N-Benzyl-N'-[1-(4-dimetbylamino-benzyl)-piperidin-4-yl]-N'-(3-methyl-but-2-enyl)-benzene-1,4-diamine;
N-Benzyl-N'-{[1-(3,3-dimethyl-butyl)]-piperidin-4-yl-N'-(3-methyl-but-2-enyl)-benzene- 1,4-diamine;
N-Benzyl-N'-[1-(4-bromo-benzyl)-piperidin-4-yl]-N'-(3-methyl-but-2-enyl)-benzene-1,4-diamine;
N-Benzyl-N'-[1-(4-methoxy-benzyl)-piperidin-4-yl]-N'-(3-methyl-but-2-enyl)-benzene-1,4-diamine;
[1-(4-Dimethylamino-benzyl)-piperidin-4-yl]-(3-methyl-but-2-enyl)-(4-phenelyl-phenyl)-amine;
(1-Benzo[1,3]dioxol-5-ylmethyl-piperidin-4-yl)-(4-benzyloxy-phenyl)-(3-methyl-but 2-enyl)-amine;
(4Benzyloxy-phenyl)-[1-(4-methanesulfinyl-benzyl)-piperidin-4-yl]-(3-methyl-but-2enyl)-amine;
(4-Benzyloxy-phenyl)-[1-(4-isopropoxy-benzyl)-piperidin-4-yl]-(3-methyl-but-2-enyl)-amine;
(4Benzyloxy-phenyl)-(3-methyl-but-2-enyl)-[1-(4-methylsulfanyl-benzyl)-piperidin-4-yl]-amine;
4Benzyloxy-phenyl)-[1-(4-ethoxy-benzyl)-piperidin-4-yl]-(3-methyl-but-2-enyl)-amine;
4Benzyloxy-phenyl)-[1-(3-methoxy-3-methyl-butyl)-piperidin-4-yl]-(3-methyl-but-2-enyl)-amine;
4Benzyloxy-phenyl)-(3-methyl-but-2-enyl)-(1-pentyl-piperidin-4-yl)-amine;
4Benzyloxy-phenyl)-[1-(3,3-dimethyl-butyl)-piperidin-4-yl]-(3-methyl-butyl)-amine;
4-Benzyloxy-phenyl)-[1-(3-methoxy-3-methyl-butyl)-piperidin-4-yl]-(3-methyl-butyl)-amine;
4-Benzyloxy-phenyl)-(3-methyl-butyl)-(1-pentyl-piperidin-4-yl)-amine;
4-[(4-Benzyloxy-phenyl)-(3-methyl-butyl)-amino]-piperidin-1-yl }-[4-methyl-1-methyl-butyl)-piperazin-2-yl]-methanone;
4-[(4-Benzyloxy-phenyl)-(3-methyl-butyl)-amino]-piperidin-1-yl }-[4-isopropyl-1-(3-methyl-butyl)-piperazin-2-yl]-methanone;
4-[(4-Benzyloxy-phenyl)-(3-methyl-butyl)-amino]-piperidin-1-yl }-[4-methyl-1-(3-methyl-butyl)-piperidin-2-yl]-methanone;
4-Benzyloxy-phenyl)-[1-(3,3-dimethyl-butyl)-piperidin-3-yl]-(3-methyl-butyl)-amine;
4-Benzyloxy-phenyl)-[1-(3-methoxy-3-methyl-butyl)-piperidin-3-yl]-(3-methyl-butyl)-amine;
4-Benzyloxy-phenyl)-(3-methyl-butyl)-(1-pentyl-piperidin-3-yl)-amine;
{3-[(4-Benzyloxy-phenyl)-(3-methyl-butyl)-amino]-piperidin-1-yl}-[4-methyl-1-3-methyl-butyl)-piperazin-2-yl]-methanone;
3-[(4-Benzyloxy-phenyl)-(3-methyl-butyl)-amino]-piperidin-1-yl}-[4-isopropyl-1-(3-methyl-butyl)-piperazin-2-yl]-methanone;
3-[(4-Benzyloxy-phenyl)-(3-methyl-butyl)-amino-piperidin-1-yl}-[4-methyl-1-(3-methyl-butyl)-piperidin-2-yl]-methanone;
4-Benzyloxy-phenyl)-[1-(3,3-dimethyl-butyl)-piperidin-3-yl]-(3-methyl-but-2-enyl)-amine;
4-Benzyloxy-phenyl)-[1-(3-methoxy-3-methyl-butyl)-piperidin-3-yl]-(3-methyl-but-2-enyl)-amine;
4-Benzyloxy-phenyl)-(3-methyl-but-2-enyl)-(1-pentyl-piperidin-3-yl)-amine;
3-[(4-Benzyloxy-phenyl)-(3-methyl-but-2-enyl)-amino]-piperidin-1-yl}-[4-methyl-1-(3-methyl-butyl)-piperazin-2-yl]-methanone;
3-[(4-Benzyloxy-phenyl)-(3-methyl-but-2-enyl)-amino]-piperidin-1-yl}-[4-isopropyl-1-(3-methyl-butyl)-piperazin-2-yl]-methanone;
3-[(4-Benzyloxy-phenyl)-(3-methyl-but-2-enyl)-amino]-piperidin-1-yl}-[4-methyl-1-(3-methyl-butyl)-piperidin-2-yl]-methanone;
4-Benzyloxy-phenyl)-[1-(3,3-dimethyl-butyl)-pyrrolidin-3-yl]-(3-methyl-but-2-enyl)-amine;
4-Benzyloxy-phenyl)-[1-(3-methoxy-3-methyl-butyl)-pyrrolidin-3-yl]-(3-methyl-but-2-enyl)-amine;

4-Benzyloxy-phenyl)-(3-methyl-but-2-enyl)-(1-pentyl-pyrrolidin-3-yl)-amine;

3-[(4-Benzyloxy-phenyl)-(3-methyl-but-2-enyl)-amino]-pyrrolidin-1-yl}-[4-methyl-1-(3-methyl-butyl)-piperazin-2-yl]-methanone;

3-[(4-Benzyloxy-phenyl)-(3-methyl-but-2-enyl)-amino]-pyrrolidin-1-yl}-[4-isopropyl-1-(3-methyl-butyl)-piperazin-2-yl]-methanone;

3-[(4-Benzyloxy-phenyl)-(3-methyl-but-2-enyl)-amino]-pyrrolidin-1-yl}-[4-methyl-1-(3-methyl-butyl)-piperidin-2-yl]-methanone;

(4-Benzyloxy-phenyl)-(1-benzyl-piperidin-4-yl)-(3-methyl-but-2-enyl)-amine;

4-{4-[(4-Benzyloxy-phenyl )-(3-methyl-but-2-enyl)-amino]-piperidin-1-yl}-butan-2-ol;

(4-Benzyloxy-phenyl)-(1-furan-2-ylmethyl-piperidin-4-yl)-(3-methyl-but-2-enyl)-amine;

(4-Benzyloxy-phenyl)-(3-methyl-but-2-enyl)-[1-(3-phenyl-propyl)-piperidin-4-yl]-amine;

(4-Benzyloxy-phenyl)-(3-methyl-but-2-enyl)-(1-phenethyl-piperidin-4-yl)-amine;

(4-Benzyloxy-phenyl)-[1-(4-methanesulfonyl-benzyl)-piperidin-4-yl]-(3-methyl-but-2-enyl)-amine;

(4-Benzyloxy-phenyl)-[1-(4-fluoro-benzyl)-piperidin-4-yl]-(3-methyl-but-2enyl)-amine;

[1-(3,3-Dimethyl-butyl)-piperidin-4yl]-(4-isopropyl-phenyl)-(3-methyl-but-2-enyl)-amine;

4-{4-[(4-Isopropyl-phenyl)-(3-methyl-but-2-enyl)-amino]-piperidin-1-yl}-butan-2-ol;

(4-Isopropyl-phenyl)-(3-methyl-but-2-enyl)-[1-(3-methyl-butyl)-piperidin-4-yl]-amine;

[1-(4-Fluoro-benzyl)-piperidin-4-yl]-(4-isopropyl-phenyl)-(3-methyl-but-2-enyl)-amine;

(4-Isopropyl-phenyl)-(3-methyl-but-2-enyl)-( 1-pyridin-3-ylmethyl-piperidin-4-yl)-amine;

[1-(1H-Imidazol-4-ylmethyl)-piperidin-4-yl]-(4-isopropyl-phenyl)-(3-methyl-but-2-enyl)-amine;

2-{4-[(4-Isopropyl-phenyl)-(3-methyl-but-2-enyl)-amino]-piperidin-1-yl}-propan-1-ol;

(4-Isopropyl-phenyl)-(3-methyl-but-2-enyl)-[1-(1H-pyrrol-2-ylmethyl)-piperidin-4-yl]-amine;

(4-Isopropoxy-phenyl)-(3-methyl-but-2-enyl)-[1-(3-methyl-butyl)-piperidin-4-yl]-amine;

[1-(4-Fluoro-benzyl)-piperidin4-yl]-(4-isopropoxy-phenyl)-(3-methyl-but-2-enyl)-amine;

1-(3,3-Dimethyl-butyl)-piperidin-4-yl]-(4-isopropoxy-phenyl)-(3-methyl-but-2-enyl)amine;

[4-(3,3-Dimethyl-butyl)-phenyl]-(3-methyl-but-2-enyl)-[1-(3-methyl-butyl)-piperidin-4-yl]-amine;

4-(3,3-Dimethyl-butyl)-phenyl]-[1-(3,3-dimethyl-butyl)-piperidin-4-yl]-(3-methyl-but-2-enyl)-amine;

[1-(4-Dimethylamino-benzyl)-piperidin-4-yl]-[4-(3,3-dimethyl-butyl)-phenyl]-(3-methyl-but-2-enyl)-amine;

(4-Cyclohexylmethoxy-phenyl)-(3-methyl-butyl)-[1-(3-methyl-butyl)-piperidin-4-yl]-amine;

4-{4-[(4-Cyclohexylmethoxy-phenyl)-(3-methyl-butyl)-amino]-piperidin-1-yl }-butan-2-ol;

(4-Cyclohexylmethoxy-phenyl)-[1-(3,3-dimethyl-butyl)-piperidin-4-yl]-(3-methyl-butyl)-amine;

[1-(3,3-Dimethyl-butyl)-piperidin-4-yl]-[4-(4-fluoro-benzyloxy)-phenyl]-(3-methyl-butyl)-amine;

(S)-1-{4-[(4-Benzyloxy-phenyl)-(3-methyl-but-2-enyl)-amino]-piperidin-1-yl}-2-hydroxy-4-methyl-pentan-1-one;

(S)-2-Hydroxy-1-{4-[(4-isopropyl-phenyl)-(3-methyl-but-2-enyl)-amino]-piperidin-1-yl}-4-methyl-pentan-1-one;

(3-Benzyloxy-phenyl)-[1-(3,3-dimethyl-butyl)-piperidin-4-yl]-(3-methyl-but-2-enyl)-amine;

[4-(3,3-Dimethyl-butyl)-phenyl]-(3-methyl-but-2-enyl)-[1-(1H-pyrrol-2-ylmethyl)-piperidin-4-yl]-amine;

[1-(3,3-Dimethyl-butyl)-piperidin-4-yl]-(3-methyl-but-2-enyl)-(4-phenethyl-phenyl)-amine;

(4-Benzyloxy-phenyl)-[1-(4-tert-butyl-benzyl)-piperidin-3-yl]-(3-methyl-but-2-enyl)-amine;

(4-Benzyloxyphenyl)-[1-(4-tert-butyl-benzyl)-piperidin-3-yl]-(3-methyl-but-2-enyl)-amine;

(1-Cyclohexylmethyl-piperidin-4-yl)-(4-isopropyl-phenyl)-(3-methyl-but-2-enyl)-amine;

(4-Isopropy-phenyl)-(3-methyl-but-2-enyl)-[1-(tetrahydro-pyran-4-yl)-piperidin-4-yl]-amine;

(1 -Cyclohexyl-piperidin-4-yl)-(4-isopropyl-phenyl)-(3-methyl-but-2-enyl)-amine;

[4-(4-Fluoro-benzyloxy)-phenyl]-(3-methyl-butyl)-[1-(3,3,3-trifluoro-propyl)-piperidin-4-yl]-amine;

(4-Cyclohexylmethoxy-phenyl)-(3-methyl-butyl)-[1-(3,3,3-trifluoro-propyl)-piperidin-4-yl]-amine;

(1-Furan-3-ylmethyl-piperidin-4-yl)-(4-isopropyl-phenyl)-(3-methyl-but-2-enyl)-amine;

(4-Isopropyl-phenyl)-(3-methyl-but-2-enyl)-(1-thiophen-3-ylmethyl-piperidin-4-yl)-amine;

[1-(3,3-Dimethyl-butyl)-piperidin-4-yl]-[4-(furan-3-ylmethoxy)-phenyl]-(3-methyl-butyl)-amine;

[1-(4-Fluoro-benzyl)-piperidin-4-yl]-[4-(furan-3-ylmethoxy)-phenyl]-(3-methyl-butyl)-amine;

[4-(Furan-3-ylmethoxy)-phenyl]-(3-methyl-butyl)-[1-(1H-pyrrol-2-ylmethyl)-piperidin-4-yl]-amnne;

[1-(4-Dimethylamino-benzyl)-piperidin-4-yl]-(4-isopropyl-phenyl)-(3-methyl-but-2-enyl)-amine;

[4-(4-Fluoro-benzyloxy)-phenyl]-[1-(4-fluoro-benzyl)-piperidin4-yl]-(3-methyl-butyl)-amine;

(4-Benzyloxy-phenyl)-(3-methyl-but-2-enyl)-(1-phenyl-piperidin-4-yl)-amine;

(4-Benzyloxy-phenyl)-[1-(4-fluoro-phenyl)-piperidin-4-yl]-(3-methyl-but-2-enyl)-amine;

(4-Benzyloxy-phenyl)-(3-methyl-but-2-enyl)-[1-(4-trifluoromethyl-phenyl)-piperidin-4-yl]-amine;

[4-(4-Fluoro-benzyloxy)-phenyl]-(3-methyl-butyl)-(1-pyridin-2-ylmethyl-piperidin-4-yl)-amine;

[4-(4-Fluoro-benzyloxy)-phenyl]-(3-methyl-butyl)-(1-pyridin-4-ylmethyl-piperidin-4-yl)-amine;

4-{4-[(4-Isopropyl-phenyl)-(3-methyl-but-2-enyl )-amino]-piperidin-1-ylmethyl}-phenol;

(4-Isopropyl-phenyl)-(3-methyl-but-2-enyl)-[1-(3,3,3-trifluoro-propyl)-piperidin-4-yl]-amine;

(4-Cyclohexylmethoxy-phenyl)-(3-methyl-butyl)-[1-(1H-pyrrol-3-ylmethyl)-piperidin-4-yl)-amine;

[4-(4-Fluoro-benzyloxy)-phenyl]-(3-methyl-butyl)-[1-(1H-pyrrol-3-ylmethyl)-piperidin-4-yl)-amine;

(trans)-2-{4-[(4-Benzyloxy-phenyl)-(3-methyl-but-2-enyl)-amino]-piperidin-1-yl }-cyclohexanol;

(4-Benzyloxy-phenyl)-(1-benzyl-piperidin-4-yl)-(3-methyl-butyl)-amine;

(4-Benzyloxy-phenyl)-(1-benzy-piperidin-4yl)-cylohexylmethyl-amine;

(4-Benzyloxy-phenyl)-(1-benzyl-piperidin4-yl)-ethyl-amine;

Benzyl-(4-benzyloxy-phenyl)-(1-benzyl-piperidin-4-yl)-amine;

(4-Benzyloxy-phenyl)-[1-(4-dimethylamino-benzyl)-piperidin-3-yl]-(3-methyl-butyl)-amine;

(4-Benzyloxy-phenyl)-(3-methyl-but-2-enyl)-[1-(1H-pyrrol-3-ylmethyl)-piperidin-3-yl]-amine;

(1-Benzyl-piperidin-4-yl)-(3-methyl-butyl)-[4-(pyridin-3-ylmethoxy)-phenyl]-amine;

(4-Benzyloxy-phenyl)-(3-methyl-but-2-enyl)-[1-(3,3,3-trifluoro-propyl)-piperidin-4-yl]-amine; and (4-Benzyloxy-phenyl)-[1-(3,3-dimethyl-butyl)-piperidin-4-yl]-(3-methyl-butyl)-amine.

Also provided is a pharmaceutical composition comprising a compound of Formula I.

Also provided is a method of blocking calcium channels, the method comprising administering to a patient in need of calcium channel blocking, a therapeutically effective amount of a compound of Formula I to block calcium channels.

In a preferred embodiment of the method, the calcium channels are N-type calcium channels.

In another embodiment, the present invention provides a method of blocking N-type calcium channels, the method comprising administering to a patient in need of N-type calcium channel blocking a therapeutically effective amount of a compound of Formula I effective to block N-type calcium channels.

The invention also provides a method of treating stroke, the method comprising administering to a patient having or having had a stroke a therapeutically effective amount of a compound of Formula I.

The invention also provides a method of preventing a stroke, the method comprising administering to a patient at risk of having a stroke a therapeutically effective amount of a compound of Formula I.

The invention also provides a method of treating cerebral ischemia, the method comprising administering to a patient having cerebral ischemia a therapeutically effective amount of a compound of Formula I.

The invention also provides a method of treating head trauma, the method comprising administering to a patient having head trauma a therapeutically effective amount of a compound of Formula I.

Also provided is a method of treating epilepsy, the method comprising administering to a patient having epilepsy a therapeutically effective amount of a compound of Formula I.

Also provided is a method of treating pain, the method comprising administering to a patient having pain a therapeutically effective amount of a compound Formula I.

Also provided is a method of treating asthma, the method comprising administering to a patient having asthma a therapeutically effective amount of a compound Formula I.

Also provided is a method of treating amyotrophic lateral sclerosis, the method comprising administering to a patient having amyotrophic lateral sclerosis a therapeutically effective amount of a compound Formula I.

DETAILED DESCRIPTION OF THE INVENTION

The present invention provides compounds having the Formula I

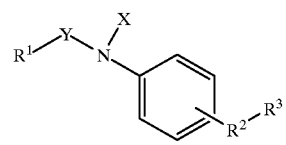

wherein
each n is independently 0 to 3;
$R_1$ is $C_1-C_8$ alkyl, substituted $C_1-C_8$ alkyl, $C_3-C_8$ cycloalkyl, substituted $C_3-C_8$ cycloalkyl, hetercycloalkyl, substituted hetercycloalkyl, $C_2-C_8$ alkenyl, $C_3-C_8$ cycloalkenyl, aryl, substituted aryl, heteroaryl, substituted heteroaryl, or arylalkyl;
Y is

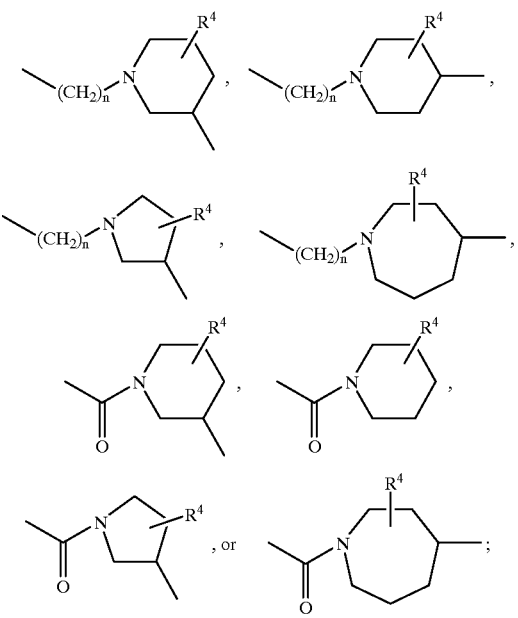

X is $C_1-C_8$ alkyl, $C_1-C_8$ substituted alkyl, $C_2-C_8$ alkenyl, substituted $C_2-C_8$ alkenyl, arylalkyl, substituted arylalkyl, heteroarylalkyl, substituted heteroarylalkyl, cycloalkylalkyl, or substituted cycloalkylalkyl;
$R^2$ is absent —O—, $(CH_2)_n$-, $O(CH_2)_n$-, $(CH_2)_nO$—, $N(R^5)(CH_2)_n$-, $(CH_2)_nN(R^5)$-, $S(CH_2)_n$-, $(CH_2)_nS$—, —C=C—, or —C≡C—;
$R^3$ is monocyclic aryl, substituted monocyclic aryl, heteroaryl, substituted heteroaryl, heterocyclic, substituted heterocyclic, $C_1-C_8$ alkyl, substituted $C_1-C_8$ alkyl, $C_3-C_{10}$ cycloalkyl, substituted $C_3-C_{10}$ cycloalkyl;
$R^4$, $R^5$ are independently H or $C_1-C_8$ alkyl; and
the pharmaceutically acceptable salts, esters, amides, and prodrugs thereof.

The term "alkyl" means a straight or branched chain hydrocarbon. Representative examples of alky groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "alkenyl" means a branched or straight chain hydrocarbon having one or more carbon-carbon double bond.

The term "aryl" means an aromatic hydrocarbon. Representative examples of aryl groups include phenyl and naphthyl.

The term "heteroatom" includes oxygen, nitrogen, and sulfur.

The term "heteroaryl" means an aryl group wherein one or more carbon atom of the aromatic hydrocarbon has been replaced with a heteroatom. Examples of heteroaryl radicals include, but are not limited to, pyridyl, imidazolyl, pyrrolyl, thienyl, furyl, pyranyl, pyrimidinyl, pyridazinyl, indolyl, quinolyl, naphthyridinyl, and isoxazolyl.

The term "cycloalkyl" means a cyclic hydrocarbon. Examples of cycloalkyl groups include cyclopropyl, cyclobutyl, cyclopentyl, and cyclohexyl.

The symbol "-" means a bond.

The term "patient" means all animals including humans. Examples of patients include humans, cows, dogs, cats, goats, sheep, and pigs.

The term "substituted" means that the base organic radical has one or more substituents. For example, substituted cyclohexyl means a cyclohexyl radical that has one or more substituents. Substituents include, but are not limited to, halogen, $C_1$–$C_8$ alkyl, —CN, —$CF_3$, —$NO_2$, —$NHC_2$, —$NHC_1$–$C_8$ alkyl,

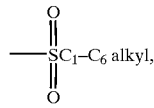

preferred substituents include, but are not limited to tert-butyl, methyl, chlorine, fluorine, bromine, —$OCH_3$, —$OCH_2CH_3$, —OH, and —$N(CH_3)_2$. Also, in the case of substituted aryl, the substituent may comprise

The term "cycloalkenyl" means a cycloalkyl group having at least one carbon-carbon double bond. Examples of cycloalkenyl groups include cyclopentene, cyclobutene, and cyclohexene.

The term "heterocycle" means a cycloalkyl group wherein one or more carbon atom is replaced with a heteroatom. Examples of heterocycles include, but are not limited to, pyrrolidinyl, piperidinyl, and piperazinyl.

Those skilled in the art are easily able to identify patients having a stroke or at risk of having a stroke; cerebral ischemia; head trauma; epilepsy; asthma; amyotrophic lateral sclerosis; or pain. For example, patients who are at risk of having a stroke include, but is not limited to patients having hypertension or undergoing major surgery.

A therapeutically effective amount is an amount of a compound of Formula I, that when administered to a patient, ameliorates a symptom of the disease.

The compounds of the present invention can be administered to a patient either alone or a part of a pharmaceutical composition. The compositions can be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragées, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977; 66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof including racemic mixtures, form part of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

In addition, it is intended that the present invention cover compounds made either using standard organic synthetic techniques, including combinatorial chemistry or by biological methods, such as through metabolism.

The examples presented below are intended to illustrate particular embodiments of the invention and are not intended to limit the scope of the specification, including the claims, in any way.

The following abbreviations are used throughout this application:

| Pr | propyl |
|---|---|
| Et | ethyl |
| HBTU | 2-(1H-benzotriazol-1yl)-1,1,3,3-tetramethyl uranium hexafluorophosphate |

| | |
|---|---|
| Bz or Bn | benzyl |
| TFA | trifluoroacetic acid |
| APCI | atmospheric pressure chemical ionization |
| NMR | nuclear magnetic resonance |
| TLC | thin layer chromatography |
| HPLC | high pressure liquid chromatography |
| DMF | dimethyl formamide |
| EtOAC | ethyl acetate |
| EtOH | ethanol |
| MS | mass spectrum |
| DCM | dichloromethane |
| $Et_3N$ | triethyl amine |
| THF | tetrahydrofuran |
| IR | infrared |
| Oac | acetate |
| bu | butyl |
| iso-pr | iso-propyl |
| FMOC | 9-fluorenylmethyloxycarbonyl |
| BOC | tertiary butyloxycarbonyl |

General Procedure for the Preparation of Calcium Channel Blockers (II):

Schemes III–VI below illustrates the preparation of the title compounds II. The preparation of intermediates I are illustrated in Schemes I and II.

Step I: The Preparation of Intermediate I

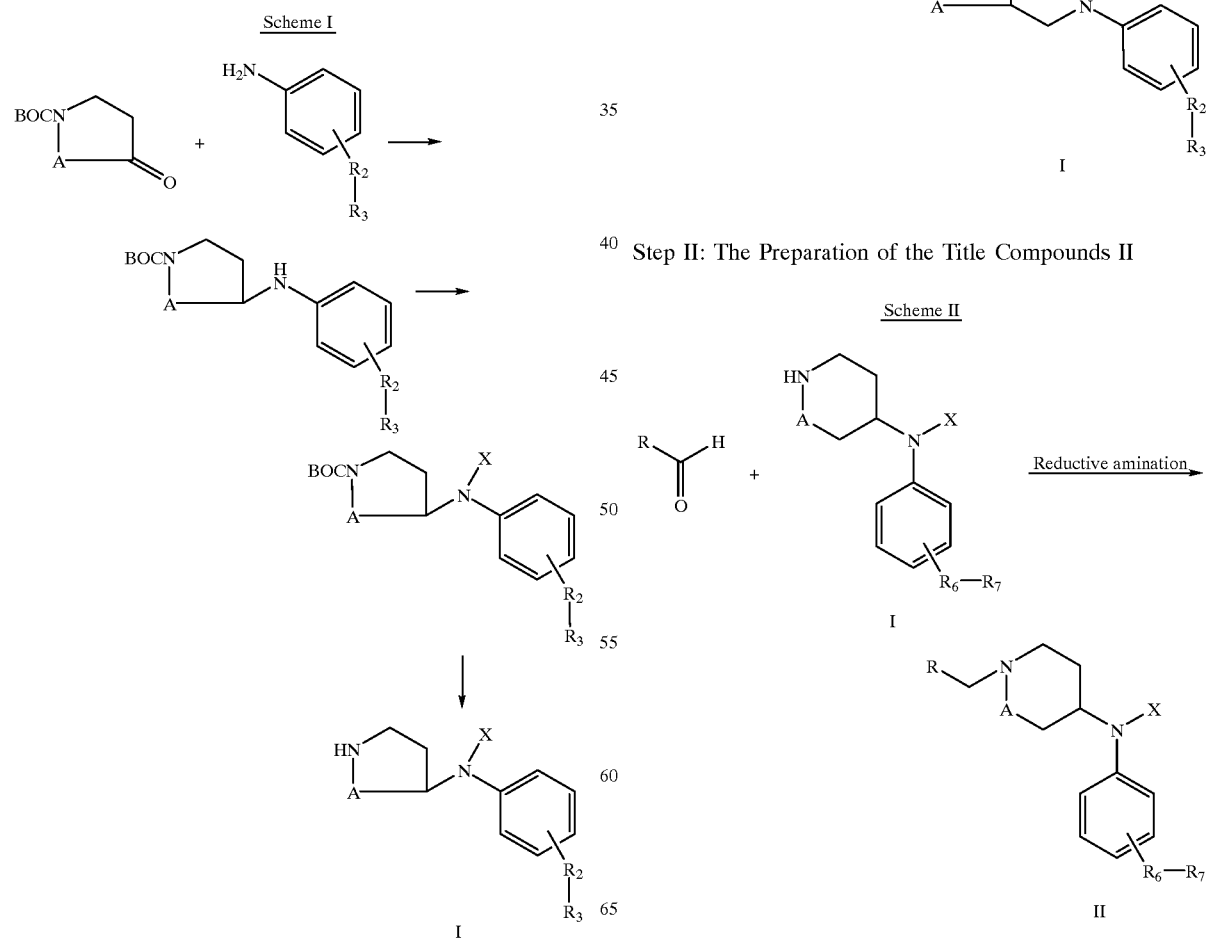

Step II: The Preparation of the Title Compounds II

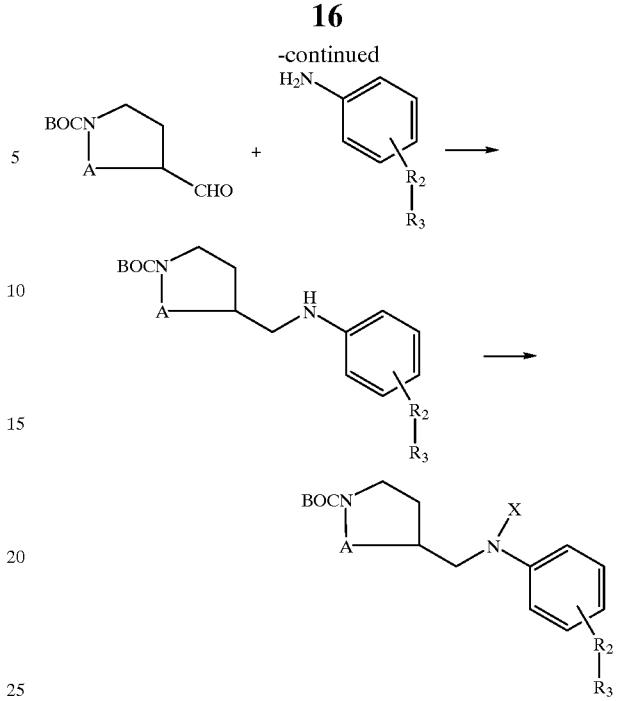

Scheme III

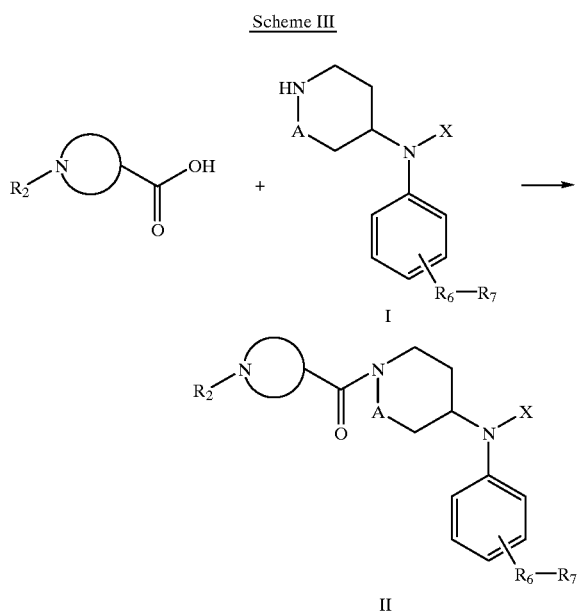

EXAMPLE 1

(4-Benzyloxy-phenyl)-(3-methyl-but-2-enyl)-[1-(3-methyl-butyl)-piperidin-4-yl]-amine

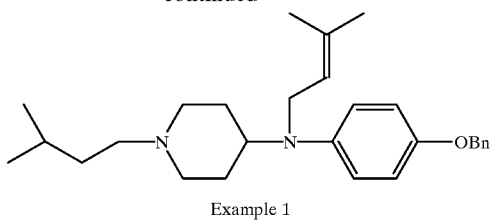

Example 1

Step 1: The preparation of 4-(4-Benzyloxy-phenylamino)-piperidine-1-carboxylic acid tert-butyl ester (Ia): 4-Benzyloxyaniline hydrochloride salt (10 g, 42.4 mmol) was suspended in EtOAc (500 mL) and washed three times with saturated sodium bicarbonate solution, once with brine, dried over $Na_2SO_4$, and concentrated. The free base was dissolved in $CH_2Cl_2$ (250 mL), treated with 1-tert-butyl-carbonyl-4-piperidone (8.45 g, 42.4 mmol), stirred for thirty minutes and then cooled to 0° C. $NaBH(OAc)_3$ (13.5 g, 63.6 mmol) was added and the reaction was allowed to warm to room temperature and stir for eighteen hours. The reaction was diluted with $CH_2Cl_2$ (250 mL), washed with saturated sodium bicarbonate solution and brine, dried over $Na_2SO_4$, and concentrated to give 15.3 g (94%) of the desired product. MS: 383 (M+1 for $C_{23}H_{30}N_2O_3$); TLC: $SiO_2$, $R_f$ 0.39 (2:1 hexane/EtOAc).

Step 2: The preparation of 4-[(4-Benzyloxy-phenyl)-(3-methyl-but-2-enyl)-amino]-piperidine-1-carboxylic acid tert-butyl ester (Ib): 4-(4-Benzyloxy-phenylamino)-

Scheme IV

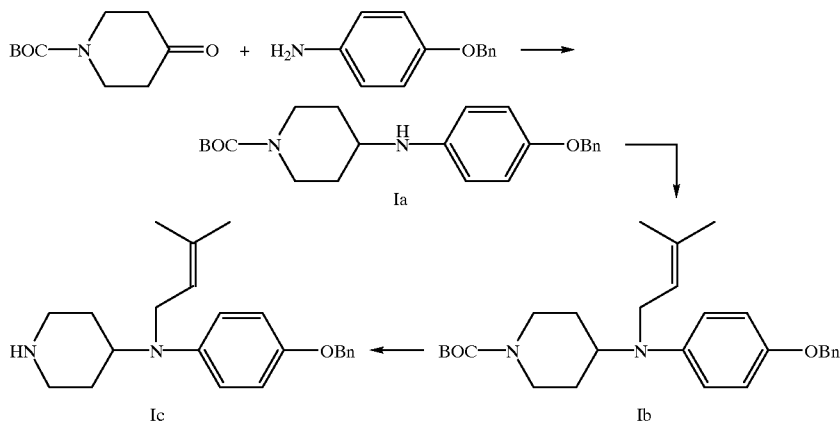

piperidine-1-carboxylic acid tert-butyl ester (5.0 g, 13.1 mmol) was dissolved in THF (65 mL), then treated with N,N-diisopropylethylamine (9.1 mL, 52.4 mmol) and 4-bromo-2-methyl]-2-butene (3.0 mL, 26.2 mmol). The reaction was heated to 40° C. for eighteen hours, then concentrated in vacuo. The residue was chromatographed on silica gel eluting with 5:1 hexane/EtOAc to give 5.15 g of the desired compound. (87% yield)

MS: 451 (M+1 for $C_{28}H_{38}N_2O_3$); TLC: $SiO_2$, $R_f$ 0.26 (5:1 hexane/EtOAc);

Analysis ($C_{28}H_{38}N_2O_3$): (Calc) C: 74.63, H: 8.50, N: 6.22 (found) C: 74.42, H: 8.50, N: 6.22.

Step 3: The preparation of (4-Benzyloxy-phenyl)-(3-methyl-but-2-enyl)-piperidin-4-yl-amine, (Ic): 4-[(4-Benzyloxy-phenyl)-(3-methyl-but-2-enyl)-amino]-

Scheme V

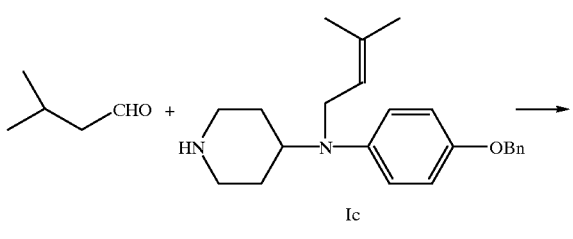

piperidine-1-carboxylic acid tert-butyl ester (5.0 g, 11.1 mmol) was dissolved in $CH_2Cl_2$ (20 mL) and treated with TFA (20 mL). The reaction was stirred for ten minutes, then concentrated in vacuo. The residue was redissolved in EtOAc (400 mL), then washed with saturated bicarbonate solution (2×400 mL) and brine (1×400 mL), dried over $Na_2SO_4$, and concentrated in vacuo to give 3.9 g (99%) of the desired product as a pale oil.

MS: 351 (M+1 for $C_{23}H_{30}N_2O_1$); TLC: $SiO_2$, $R_f$0.49 (10% MeOH/$CH_2Cl_2$).

Step 4: The preparation of Example 1. (4-Benzyloxy-phenyl)-(3-methyl-but-2-enyl)-[1-(3-methyl-butyl)-piperidin-4-yl]-amine: (4-Benzyloxy-phenyl)-(3-methyl-but-2-enyl)-piperidin-4-yl-amine (0.2 g, 0.57 mmol) was dissolved in dichloromethane and treated with isovaleraldehyde (61 µL, 0.57 mmol). The reaction was stirred for thirty minutes, then cooled to 0° C. in an ice bath and treated with NaBH(OAc)$_3$ (0.18 g, 0.86 mmol). The reaction was allowed to warm to room temperature as the ice melted and stirred for eighteen hours at room temperature. The reaction was diluted with EtOAc (125 mL), then washed with saturated bicarbonate (125 mL) and brine (125 mL), dried over $Na_2SO_4$, and concentrated. The residue was chromatographed on silica gel eluting with 7% MeOH/$CH_2Cl_2$ to give 0.17 g of the title compound. Yield: 71%.

MS: 421 (M+1 for $C_{28}H_{40}N_2O_1$); mp: 170° C. dec.; TLC: $SiO_2$, $R_f$0.22 (5% MeOH/$CH_2Cl_2$); Analysis ($C_{28}H_{40}N_2O_1 \times 0.25H_2O$) (Cal.) C: 79.10, H: 9.60, N: 6.59 (found) C: 78.83, H: 9.46, N: 6.67.

Example 2

(4-Benzyloxy-phenyl)-[1-(3,3-dimethyl-butyl)-piperidin-4-yl]-(3-methyl-but-2-enyl)-amine was made in accordance with the process of Example 1 (Step 4), except that 3,3-dimethylbutyralaldehyde was used instead of isovaleraldehyde.

Yield: 54%

MS: 435 (M+for $C_{29}H_{42}N_2O_1$); an oil; TLC: $R_f$=0.2 ($SiO_2$, EtOAc/Hexanes);

Analysis ($C_{29}H_{42}N_2O_1$): (Cal.) C: 80.13, H 9.74, N: 6.45, (found) C: 79.82, H: 9.92, N: 6.28.

Example 3

(4-Benzyloxy-phenyl)-[1-(4-tert-butyl-benzyl)-piperidin-4-yl]-(3-methyl-but-2-enyl)-amine was made in accordance with the process of Example 1 (Step 4), except that 4-tert-butyl-benzaldehyde was used instead of isovaleraldehyde. Yield 76%.

MS: 497 (M+1 for $C_{34}H_{44}N_2O_1$); sticky solid; TLC: $SiO_2$, $R_f$0.38 (8% MeOH/$CH_2Cl_2$); Analysis ($C_{34}H_{44}N_2O_1$): (Cal.) C: 82.21, H: 8.93, N: 5.64 (found) C: 81.99, H: 9.02, N: 5.29.

Example 4

(4-Benzyloxy-phenyl)-[1-(4-bromo-benzyl)-piperidin4-yl]-(3-methyl-but-2-enyl)-amine was made in accordance with the process of Example 1 (Step 4), except that 4-bromobenzaldehyde was used instead of isovaleraldehyde. Yield: 40%

MS: 521 (M+for $C_{30}H_{35}N_2O_1Br_1$); an oil; TLC: $SiO_2$, $R_f$=0.8 (50% EtOAc/Hexanes);

Analysis ($C_{30}H_{35}N_2O_1Br_1 \times H_2O$): (Cal.) C: 67.03, H:6.94, N: 5.21, (found) C: 67.03, H:6.62, N: 4.82.

Example 5

4-{4-[(4-Benzyloxy-phenyl)-(3-methyl-but-2-enyl)-amino]-piperidin-1-ylmethyl}-phenol was made in accordance with the process of Example 1 (Step 4), except that 4-hydroxybenzaldehyde was used instead of isovaleraldehyde. Yield: 31%.

MS: 457 (M+1 for $C_{30}H_{36}N_2O_2$); sticky solid; TLC: $SiO_2$, $R_f$0.55 (10% MeOH/$CH_2Cl_2$);

Analysis ($C_{30}H_{36}N_2O_2 \times 0.25H_2O$) (Cal.) C: 78.14, H: 7.98, N: 6.08 (found) C: 78.39, H: 7.70, N: 6.00.

Example 6

(4-Benzyloxy-phenyl)-[1-(4-dimethylamino-benzyl)-piperidin-4-yl]-(3-methyl-but-2-enyl)-amine was made in accordance with the process of Example 1 (Step 4), except that 4-dimethylaminobenzaldehyde was used instead of isovaleraldehyde. Yield: 18%.

MS: 484 (M+1 for $C_{32}H_{41}N_3O_1$); sticky solid; TLC: $SiO_2$, $R_f$0.35 (6% MeOH/$CH_2Cl_2$);

Analysis ($C_{32}H_{41}N_3O_1 \times 0.25H_2O$): (Cal.) C: 78.72, H: 8.57, N: 8.61 (found) C: 78.98, H: 8.61, N: 8.59.

Example 7

(4-Benzyloxy-phenyl)-(3-methyl-but-2-enyl)-[1-(1H-pyrrol-2-ylmethyl)-piperidin-4-yl]-amine was made in accordance with the process of Example 1 (Step 4), except that pyrrole-2-carboxaldehyde was used instead of isovaleraldehyde.

MS: 430 (M+1 for $C_{28}H_{35}N_3O_1$); sticky solid; TLC: $SiO_2$, $R_f$0.42 (8% MeOH/$CH_2Cl_2$);

HPLC: 100% pure, RT=3.09 min. (C-18 column, 1:1 $CH_3CN/H_2O$ with 0.5% TFA, 0.75 mL/min).

Example 8

(4-Benzyloxy-phenyl)-[1(1H-imidazol-4-ylmethyl)-piperidin-4-yl]-(3-methyl-but-2-enyl)-amine was made in accordance with the process of Example 1 (Step4), except that 4-formylimidazole was used instead of isovaleraldehyde. Yield: 53%

MS: 431 (M+for $C_{27}H_{34}N_4O_1$); sticky solid; TLC: $SiO_2$ $R_f$=0.2 (10% MeOH/$CH_2Cl_2$); Analysis ($C_{27}H_{34}N_4O_1 \times H_2O$): (Cal.) C: 72.29, H: 8.09, N: 12.49, (found) C: 72.07, H: 7.87, N: 12.17.

Example 9

(4-Benzyloxy-phenyl)-(3-methyl-but-2-enyl)-(1-pyridin-2-ylmethyl-piperidin-4-yl)-amine was made in accordance with the process of Example 1 (Step 4), except that pyridine-2-carboxaldehyde was used instead of isovaleraldehyde. Yield: 66%.

MS: 442 (M+1 for $C_{29}H_{35}N_3O_1$); mp 132–134° C.; TLC: $SiO_2$, $R_f$0.18 (5% MeOH/$CH_2Cl_2$); Analysis ($C_{29}H_{35}N_3O_1$): (Calc.) C: 78.87, H: 7.99, N: 9.51 (found) C: 78.55, H: 8.17, N: 9.43.

Example 10

(4-Benyloxy-phenyl)-(3-methyl-but-2-enyl)-[1-(tetrahydro-pyran4-yl)-piperidin-4-yl]-amine was made in accordance with the process of Example 1 (Step 4), except that tetrahydropyran-4-one was used instead of isovaleraldehyde. Yield: 41%.

MS: 435 (M+1 for $C_{28}H_{38}N_2O_2$); sticky solid; TLC: $SiO_2$, $R_f$0.29 (5% MeOH/$CH_2Cl_2$);

HPLC: 100% pure, RT=3.34 min. (C-18 column, 1:1 $CH_3CN/H_2O$ with 0.5% TFA, 0.75 mL/min).

Example 11

{4-[(4-Benzyloxy-phenyl)-(3-methyl-but-2-enyl)-amino]-piperidin-1-yl}-[1-(3-methyl-butyl)-piperidin-2-yl]-methanone Step 1: The preparation of piperidine-2-carboxylic acid: Pyridine-2-carboxylic acid (10.0 g, 81.3 mmol) was treated with $H_2O$ (100 mL), $NH_4OH$ (10 mL), and 20% Pd/C (2.0 g) and shaken under an atmosphere of $H_2$. The reaction was filtered and concentrated to give 10 g (95%) of the desired product.

MS: 130 (M+1 for $C_6H_{11}N_1O_2$).

Step 2: The preparation of 1-(3-methyl-butyl)-piperidine-2-carboxylic acid: Piperidine-2-carboxylic acid (4.0 g, 30 mmol) was treated with EtOH (100 mL), isovaleraldehyde (6.6 mL, 60 mmol), and 20% Pd/C (1.0 g) and shaken under an atmosphere of $H_2$ for twenty-three hours. The reaction was filtered and concentrated to dryness, then twice stirred with acetone (100 mL) for 1 hour and filtered. The solid was dried under vacuum to give 5.0 g of the desired product.

MS: 200 (M+1 for $C_{11}H_{21}N_1O_2$); mp 230–231° C.;

Analysis (calc) C: 66.29, H: 10.62, N: 7.03 (found) C: 66.07, H: 10.23, N: 6.84.

Step 3: The preparation of Example 11: {4-[(4-Benzyloxy-phenyl)-(3-methyl-but-2-enyl)-amino]-piperidin-1-yl}-[1(3-methyl-butyl)-piperidin-2-yl]-methanone: (4-Benzyloxy-phenyl)-(3-methyl-but-2-enyl)-piperidin-4-yl-amine (0.175 g, 0.50 mmol) was dissolved in DMF (5 mL). Diisopropylethylamine (0.26 mL, 1.5 mmol) and N-isopentylpiperidine-2-arboxylic acid (0.1 g, 0.50 mmol) were added, followed by HBTU (0.19 g, 0.50 mmol). The reaction was stirred for 5 hours at room temperature, then diluted with EtOAc (125 mL), washed with saturated sodium bicarbonate solution and brine, dried over $Na_2SO_4$, and concentrated. The residue was chromatographed on silica gel eluting with 4% $MeOH/CH_2Cl_2$ to give 91 mg (34%) of the title compound.

MS: 532 (M+1 for $C_{34}H_{49}N_3O_2$); sticky solid; TLC: $SiO_2$, $R_f$ 0.49 (6% $MeOH/CH_2Cl_2$);

Analysis ($C_{34}H_{49}N_3O_2 \times 0.25 H_2O$) (Cal.) C: 76.15, H: 9.30, N: 7.84 (found) C: 76.00, H: 9.31, N: 7.87.

Example 12

{4-[(4-Benzyloxy-phenyl)-(3-methyl-but-2-enyl)-amino]-piperidin-1-yl}-[1-(3-methyl-butyl)-piperidin-3-yl]-methanone Step 1: The preparation of 1-(3-Methyl-butyl)-piperidine-3-carboxylic acid: Piperidine-3-carboxylic acid (19.8 g, 153 mmol) was treated with EtOH (400 mL), isovaleraldehyde (33 mL, 307 mmol), and 20% Pd/C (2.0 g). The reaction was shaken under $H_2$, then filtered and concentrated to dryness and further dried in vacuo. The crude material was treated with acetone, stirred, and filtered three times. The solid obtained was dried in vacuo to give 22.0 g (72%) of the desired product.

MS: 200 (M+1 for $C_{11}H_{21}N_1O_2$);

Step 2: The preparation of Example 12: {4[(4-Benzyloxy-phenyl)-(3-methyl-but-2-enyl)-amino]-piperidin-1-yl}-[1-(3-methyl-butyl)-piperidin-3-yl]-methanone was made in accordance with the process of Example 11 (Step 3), except 1-(3-Methyl-butyl)-piperidine-3-carboxylic acid was used instead of 1-(3-Methyl-butyl)-piperidine-2-carboxylic acid.

MS: 532 (M+1 for $C_{34}H_{49}N_3O_2$); sticky solid; TLC: $SiO_2$, $R_f$ 0.3 (20% $MeOH/CH_2Cl_2$);

Analysis ($C_{34}H_{49}N_3O_2 \times 0.5 H_2O$) (Cal.) C: 75.52, H: 9.32, N: 7.70 (found) C: 75.62, H: 9.25, N: 7.91.

Example 13

{4-[(4-Benzyloxy-phenyl)-(3-methyl-but-2-enyl)-amino]-piperidin-1-yl}-[1-(3-methyl-butyl)-piperidin4-yl]-methanone Step 1: The preparation of 1-(3-Methyl-butyl)-piperidine-4-carboxylic acid: Piperidine-4-carboxylic acid (10.0 g, 77.4 mmol) was dissolved in EtOH (400 mL) and treated with isovaleraldehyde (17 mL, 155 mmol) and 20% Pd/C (1.0 g). The reaction mixture was shaken under an atmosphere of $H_2$ (50 psi) for twenty hours. The reaction was filtered through Celite and concentrated in vacuo to give 15.75 g (97%) of the desired product as a white solid.

MS: 200 (M+1 for $C_{11}H_{21}N_1O_2$).

Step 2: The preparation of Example 13: 1-(3-Methyl-butyl)-piperidine-4-carboxylic acid (0.1 g, 0.50 mmol) was dissolved in DMF (5 mL) and treated with (4-Benzyloxy-phenyl)-(3-methyl-but-2-enyl)-piperidin-4-yl-amine (0.175 g, 0.50 mmol), diisopropylethylamine (0.26 mL, 1.5 mmol), and HBTU (0.19 g, 0.50 mmol). The reaction was stirred for 4 hours, then diluted with EtOAc (125 mL), washed with saturated sodium bicarbonate solution and brine, dried over $Na_2SO_4$, and concentrated. The residue was chromatographed on silica gel eluting with 8% $MeOH/CH_2Cl_2$ to give 47 mg (18%) of {4-[(4-Benzyloxy-phenyl)-(3-methyl-but-2-enyl)-amino]-piperidin-1-yl }-[1-(3-methyl-butyl)-piperidin-4-yl]-methanone.

MS: (M+1 for $C_{34}H_{49}N_3O_2$); sticky solid; TLC: $SiO_2$, $R_f$ 0.32 (8% $MeOH/CH_2Cl_2$);

HPLC: 97% pure, RT=6.12 min (C-18 column, gradient over ten minutes: 10:90 to 98:2 $CH_3CN/H_2O$ with 0.1% formiic acid, 1.0 mL/min).

Example 14

{4-[(4-Benzyloxy-phenyl)-(3-methyl-but-2-enyl)-amino]-piperidin-1-yl}-[4-methyl-1-(3-methyl-butyl)-piperazin-2-yl]-methanone Step 1: The preparation of piperazine-2-carboxylic acid: Pyrazine-2-carboxylic acid (102.7 g, 0.827 mol) was dissolved in $H_2O$ (600 mL), treated with NaOH (66 g, 1.65 mol) and 20% Pd/C (5.0 g), and hydrogenated for fifteen hours. The reaction was filtered and concentrated. Concentrated HCl was added to the solution and a white precipitate formed. The solid was washed with cold $H_2O$, collected by filtration and dried in vacuo to give 137.2 g (99.6%) of the desired product as the HCl salt.

MS: 131 (M+1 for $C_5H_{10}N_2O_2$).

Step 2: The preparation of piperazine-1,2,4-tricarboxylic acid 1-benzyl ester 4-tert-butyl ester: Piperazine-2-carboxylic acid (37.5 g, 185 mmol) was dissolved in $H_2O$ (600 mL) and dioxane (600 mL). The solution was adjusted to pH 11 by the addition of 50% NaOH. 2-(t-butoxycarbonyloxyimino)-2-phenylacetonitrile (51.0 g, 210 mmol) in dioxane (300 mL) was added portionwise. The reaction was maintained at pH 11 by the addition of 50% NaOH over 3 hours, then cooled to 0° C. in an ice bath and adjusted to pH 9.5 with 6 N HCl. To the cooled solution was added benzylchloroformate dropwise while maintaining the pH at 9.5. The reaction was allowed to warm to room temperature and stir for 2.5 days. The reaction was extracted with $Et_2O$ (4×250 mL), then the aqueous layer was acidified to pH 2 with concentrated HCl and extracted with EtOAc (4×250 mL). The EtOAc layer was dried over $MgSO_4$ and concentrated to give 64.2 g (95%) of the desired product.

MS: 365 (M+1 for $C_{18}H_{24}N_2O_6$).

Step 3: The preparation of piperazine-1,2,4-tricarboxylic acid, 4-(1,1-dimethylethyl) 2-methyl 1-(phenylmethyl) ester: Piperazine-1,2,4-tricarboxylic acid 1-benzyl ester 4-tert-butyl ester (20.7 g, 56.9 mmol) was dissolved in THF (100 mL) and cooled. A solution of diazomethane in $Et_2O$ was added until a yellow color persisted. The reaction was quenched with acetic acid and concentrated. The residue was dissolved in heptane/toluene (1:1) and gave 12.0 g of the desired product on overnight standing.

MS: 379 (M+1 for $C_{19}H_{26}N_2O_6$); mp: 85–86° C.; TLC: $R_f$0.26 (1:1 $Et_2O$/heptane); Analysis (calc) C: 60.31, H: 6.93, N: 7.40 (found) C: 60.58, H: 6.99, N: 7.43.

Step 4: The preparation of piperazine-1,3-dicarboxylic acid 1-tert-butyl ester 3-methyl ester: Piperazine-1,2,4-tricarboxylic acid, 4-(1,1-dimethylethyl) 2-methyl 1-(phenylmethyl) ester (9.0 g, 23.8 mmol) was treated with MeOH (100 mL) and 20% Pd/C (1.0 g) and shaken under an atmosphere of $H_2$. The reaction was filtered and concentrated to give 6.0 g (99%) of the desired product.

MS: 245 (M+1 for $C_{11}H_{20}N_2O_4$).

Step 5: The preparation of 4-(3-Methyl-butyl)-piperazine-1,3-dicarboxylic acid 1-tert-butyl ester 3-methyl ester: Piperazine-1,3-dicarboxylic acid 1-tert-butyl ester 3-methyl ester (6.0 g, 24.6 mmol) was treated with EtOH (100 mL), isovaleraldehyde (5.3 mL, 50 mmol), and 20% Pd/C (1.0 g), then shaken under an atmosphere of $H_2$. The reaction was filtered and concentrated. The residue was chromatographed on silica gel eluting with 2:1 hexanes/EtOAC to give 7.0 g (90%) of the desired product as an oil.

MS: 316 (M+1 for $C_{16}H_{30}N_2O_4$); colorless liquid; TLC: $SiO_2$, $R_f$0.8 (50% hexanes/EtOAc);

Analysis: ($C_{16}H_{30}N_2O_4$) (calc.) C: 61.12, H: 9.62, N: 8.91; (found) C: 61.00, H: 9.54, N: 8.54.

Step 6: The preparation of 1-(3-Methyl-butyl)-piperazine-2-carboxylic acid methyl ester: 4-(3-Methyl-butyl)-piperazine-1,3-dicarboxylic acid 1-tert-butyl ester 3-methyl (5.89 g, 18.4 mmol) was dissolved in $CH_2Cl_2$ (35 mL) and treated with TFA (35 mL). The reaction was stirred for 30 minutes, then concentrated in vacuo. The residue was dissolved in EtOAc, washed with saturated sodium bicarbonate solution, dried over powdered sodium bicarbonate, and concentrated to give 4.3 g of the desired product.

MS: 215 (M+1 for $C_{11}H_{22}N_2O_2$); colorless liquid; TLC: $SiO_2$, $R_f$0.4 (5% MeOH/EtOAc).

Step 7: The preparation of 4-Methyl-1-(3-methyl-butyl)-piperazine-2-carboxylic acid methyl ester: 1-(3-Methyl-butyl)-piperazine-2-carboxylic acid methyl ester (1.5 g, 7 mmol) was dissolved in MeOH (50 mL), treated with 37% HCHO (1.7 g, 14 mmol), and 10% Pd/C (0.3 g), and shaken under an atmosphere of $H_2$. The reaction was filtered and concentrated. The residue was chromatographed on silica gel eluting with 20:1 EtOAc/MeOH to give 1.3 g (81%) of the desired product.

MS: 229 (M+1 for $C_{12}H_{24}N_2O_2$); colorless liquid; ; TLC: $SiO_2$, $R_f$0.3 (5% MeOH/EtOAc).

Step 8: The preparation of 4-Methyl-1-(3-methyl-butyl)-piperazine-2-carboxylic acid: 4-Methyl-1-(3-methyl-butyl)-piperazine-2-carboxylic acid methyl ester (1.0 g, 4.4 mmol) was treated with acetone (20 mL), water (14 mL), and concentrated HCl (6 mL), and refluxed for 34 hours. The reaction was concentrated to give 0.9 g (95%) of the desired product.

MS: 215 (M+1 for $C_{11}H_{22}N_2O_2$).

Step 9: The preparation of Example 14: Example 14 was made in accordance with the process of Example 11 (Step 3), except that 4-Methyl-1-(3-methyl-butyl)-piperazine-2-carboxylic acid was used instead of 1-(3-Methyl-butyl)-piperidine-2-carboxylic acid.

MS: 547 (M+1 for $C_{34}H_{50}N_4O_2$); sticky solid; TLC: $SiO_2$, $R_f$0.3 (20% MeOH/$CH_2Cl_2$);

Analysis ($C_{34}H_{50}N_4O_2$) (Cal.) C: 74.68, H: 9.22, N: 10.25 (found) C: 74.34, H: 9.16, N: 10.00.

Example 15

{4-[(4-Benzyloxy-phenyl)-(3-methyl-but-2-enyl)-amino]-piperidin-1-yl}-[4-isopropyl-1-(3-methyl-butyl)-piperazin-2-yl]-methanone Step 1: The preparation of 4-Isopropyl- 1-(3-methyl-butyl)-piperazine-2-carboxylic acid methyl ester: The compound was prepared in accordance with the process of Steps 1–3 in Example 14, except that acetone was used instead of formaldehyde in Step 3.

MS: 257 (M+1 for $C_{14}H_{28}N_2O_2$); oil; TLC: $SiO_2$, $R_f$0.5 (5% MeOH/EtOAc).

Step 2: The preparation of 4-Isopropyl-1-(3-methyl-butyl)-piperazine-2-carboxylic acid: The compound was made in accordance with the process of Step 4 in Example 14, except that 4-Isopropyl-1-(3-methyl-butyl)-piperazine-2-carboxylic acid methyl ester was used instead of 4-Methyl-1-(3-methyl-butyl)-piperazine-2-carboxylic acid methyl ester.

MS: 243 (M+1 for $C_{13}H_{26}N_2O_2$).

Step 3: The preparation of Example 15: {4-[(4-Benzyloxy-phenyl)-(3-methyl-but-2-enyl)-amino]-piperidin-1-yl}-[4-isopropyl-1-(3-methyl-butyl)-piperazin-2-yl]-methanone is made in accordance with the process of Example 11 (Step 3), except that 4-Isopropyl-1-(3-methyl-butyl)-piperazine-2-carboxylic acid was used instead of 1-(3-Methyl-butyl)-piperidine-2-carboxylic acid.

MS: 575 (M+1 for $C_{36}H_{54}N_4O_2$); sticky solid; TLC: $SiO_2$, $R_f$0.2 (20% MeOH/$CH_2Cl_2$);

Anays ($C_{36}H_{54}N_4O_2 \times 0.5H_2O$) (Cal.) C: 74.06, H: 9.51, N: 9.60 (found) C: 73.90, H: 9.37, N: 9.87.

Example 16

{4-[(4Benzyloxy-phenyl)-(3-methyl-but-2-enyl) amino]-piperidin-1-yl}-[6-methyl-1-(3-methyl-butyl)-piperidin-2-yl]-methanone Step 1: The preparation of 6-Methyl-piperidine-2-carboxylic acid: The compound was made in accordance with the process in Example 11 (Step 1), except that 6-methyl-pyridine-2-carboxylic acid was used instead of pyridine-2-carboxylic acid.

MS: 140 (M+1 for $C_7H_7N_1O_2$).

Step 2: The preparation of 6-Methyl-1-(3-methyl-butyl)-piperidine-2-carboxylic acid: The compound was made in accordance with the process in of Step 2 in Example 11, except that 6-Methyl-piperidine-2-carboxylic acid was used instead of piperidine-2-carboxylic acid.

MS: 214 (M+1 for $C_{12}H_{23}N_1O_2$).

Step 3: The preparation of Example 16: {4-[(4-Benzyloxy-phenyl)-(3-methyl-but-2-enyl)-amino]-piperidin-1-yl}-[6methyl-1-(3-methyl-butyl)-piperidin-2-yl]-methanone was made in accordance with the process in Step 3 in Example 11, except that 6-Methyl-1-(3-methyl-butyl)-piperidine-2-carboxylic acid was used instead of 1-(3-Methyl-butyl)-piperidine-2-carboxylic acid. The final product was further prepared as a HCl salt.

MS: 546 (M+1 for $C_{35}H_5N_3O_2$); mp 184–188° C.; TLC: $SiO_2$, $R_f$0.5 (10% MeOH/$CH_2Cl_2$) for the free base.

Example 17

{4-[(4-Benzyloxy-phenyl)-(3-methyl-but-2-enyl)-amino]-piperidin-1-yl}-[4-methyl-1-(3-methyl-butyl)-piperidin-2-yl)-methanone Step 1. The preparation of 4-methyl-2-cyano-pyridine: 4-Picoline-N-oxide (10.0 g, 91.6 mmol) was dissolved in $CH_2Cl_2$ (92 mL) and dried over $MgSO_4$. The drying agent was filtered away and the solution was added to trimetbylsilyl cyanide (11.5 g, 116 mmol). A solution of dimethylcarbamoyl chloride (12.5 g, 116 mmol) in $CH_2Cl_2$ (25 mL) was added dropwise over 45 minutes. The reaction was stirred overnight. A 10% solution of $K_2CO_3$ in water (100 mL) was added dropwise and stirred for ten minutes. The layers were separated, then the aqueous layer was washed with $CH_2Cl_2$ (2×100 mL). The organic layers were combined, dried over $Na_2SO_4$, and concentrated to give the desired product (13.18 g crude material).

MS: 119 (M+1 for $C_7H_6N_2$); $^1$HNMR ($CDCl_3$)δ2.28 (s, 3 H), 7.18 (d, 1 H, J=4.9 Hz), 7.37 (s,1 H), 8.41 (d, 1 H, J=5.1 Hz).

Step 2. The preparation of 4-methyl-pyridine-2-carboxylic acid: 4-Methyl-2-cyano-pyridine (13.0 g, 110 mmol) was treated with 6N HCl and heated to reflux for twenty hours. The reaction was concentrated to give the desired product.

MS: 138 (M+1 for $C_8H_{11}N_1O_2$); $^1$HNMR (DMSO-$d_6$) δ2.43 (s, 3 H), 7.61 (dd, 1 H, J=5.4, 1.0 Hz), 7.99 (d, 1 H, J=1.0 Hz), (8.57 (d, 1 H, J=5.4 Hz).

Step 3. The preparation of 4-methyl-pyridine-2-carboxylic acid methyl ester: 4-Methyl-pyridine-2-carboxylic acid (4.39 g, 25.3 mmol) was suspended in THF. A solution of diazomethane (60 mL, 0.43 M) in THF was added dropwise and the reaction was stirred for three hours. Several drops of AcOH were added to quench the reaction, then saturated bicarbonate solution was added. The reaction was diluted with EtOAc and the layers were separated. The aqueous layer was washed twice with EtOAc and the organic layers were combined, dried over $Na_2SO_4$, and concentrated. The residue was chromatographed on silica gel eluting with 4% $MeOH/CH_2Cl_2$ to give 1.17 g (31%) of the desired product as an oil.

MS: 152 (M+1 for $C_8H_9N_1O_2$); $^1$HNMR ($CDCl_3$)δ2.40 (s, 3 H), 3.97 (s, 3 H), 7.26 (d, 1 H, J=4.2 Hz), 7.94 (s, 1 H), 8.56 (d, 1 H, J=4.9 Hz).

Step 4. The preparation of 4-methyl-1-(3-methyl-butyl)-piperidine-2-carboxylic acid methyl ester: 4-Methyl-pyridine-2-carboxylic acid methyl ester (1.17 g, 7.74 mmol) was dissolved in acetic acid (50 mL), treated with $PtO_2$ (0.5 g), and shaken under an atmosphere of $H_2$ (50 psi) for thirty hours. The reaction mixture was evaporated under reduced pressure, then redissolved in EtOH (50 mL), treated with isovaleraldehyde (0.5 mL, 15 mmol) and 20% Pd/C (0.2 g), and shaken under $H_2$ (50 psi) for twenty hours. The reaction was filtered and concentrated in vacuo. The residue was chromatographed on silica gel eluting with 10% MeOH/ $CH_2Cl_2$ to give 1.36 g (77%) of the desired product.

MS: 228 (M+1 for $C_{13}H_{15}N_1O_2$).

Step 5. The preparation of 4-Methyl-1-(3-methyl-butyl)-piperidine-2-carboxylic acid: 4-Methyl-1-(3-methyl-butyl)-piperidine-2-carboxylic acid methyl ester (1.36 g, 5.98 mmol) was dissolved in a mixture acetone (40 mL) and water (28 mL), treated with concentrated HCl (12 mL) and heated to 95° C. overnight. Another 5 mL of concentrated HCl was added and the reaction was heated for another seventy-two hours. The reaction was cooled to room temperature and concentrated in vacuo to give 1.18 g (93%) of the desired product.

MS: 214 (M+1 for $C_{12}H_{23}N_1O_2$).

Step 6: The preparation of Example 17: {4-[(4-Benzyloxy-phenyl)-(3-methyl-but-2-enyl)-amino]-piperidin-1-yl }-[4-methyl-1-(3-methyl-butyl)-piperidin-2-yl]-methanone was made in accordance with the process of Example 11 (Step 3), except that 4-Methyl-1-(3-methyl-butyl)-piperidine-2-carboxylic acid was used instead of 1-(3-Methyl-butyl)-piperidine-2-carboxylic acid (14% yield).

MS: 546 (M+1 for $C_{35}H_{51}N_3O_2$); sticky solid; TLC: $SiO_2$, $R_f$0.45 (7% $MeOH/CH_2Cl_2$);

HPLC: 100% pure, RT=6.73 min. (C-18 column, gradient over 10 min.: 10:90 to 98:2 $CH_3CN/H_2O$ with 0.1% formic acid, 1.0 mL/min).

Example 18

{4-[(4-Benzyloxy-phenyl)-(3-methyl-but-2-enyl)-amino]-piperidin-1-yl}-[3-methyl-1-(3-methyl-butyl)-piperidin-2-yl]-methanone Step 1: 3-methyl-piperidine-2-carboxylic acid was prepared by the method of Step 1 in Example 11, except that 3-methyl-pyridine-2-carboxylic acid was used instead of pyridine-2-carboxylic acid.

MS: 144 (M+1 for $C_7H_{13}N_1O_2$).

Step 2: 3-Methyl-1-(3-methyl-butyl)-piperidine-2-carboxylic acid was prepared by the method of Step 2 in Example 11, except that 3-methyl-piperidine-2-carboxylic acid was used instead of piperidine-2-carboxylic acid.

MS: 214 (M+1 for $C_{12}H_{23}N_1O_2$); a solid.

Step 3: The preparation of Example 18: {4-[(4-Benzyloxy-phenyl)-(3-methyl-but-2-enyl)-amino]-piperidin-1-yl}-[3-methyl-1-(3-methyl-butyl)-piperidin-2-yl]-methanone was made in accordance with the process of Example 11 (Step 3), except that 3-Methyl-1-(3-methyl-butyl)-piperidine-2-carboxylic acid was used instead 1-(3-Methyl-butyl)-piperidine-2-carboxylic acid. The final product was further prepared as a HCl salt.

MS: 546 (M+1 for $C_{35}H_{51}N_3O_2$); mp 176–180° C.; TLC: $SiO_2$, $R_f$0.2 (10% $MeOH/CH_2Cl_2$) for the free base;

Analysis ($C_{35}H_{51}N_3O_2$×2HCl×2.5$H_2O$) (Cal.) C: 63.34, H: 8.80, N: 6.33 (found) C: 63.29, H: 8.71, N: 6.01.

Example 19

(4-Benzyloxy-phenyl)-(1-benzyl-piperidin4-yl)-(3-methyl-but-2-enyl)-amine was prepared in accordance with the methods of Example 1 (Steps 1–4), except that benzaldehyde was used instead of isovaleraldehyde in Step 4.

MS: 441.3 (M+1 for $C_{30}H_{36}N_2O_1$); an oil; TLC: $SiO_2$, $R_f$0.21 (3:1 hexanes/EtOAc);

Analysis ($C_{30}H_{36}N_2O_1$); (Calc) C: 81.78, H: 8.24, N: 6.36, (found) C: 81.77, H: 8.24, N: 6.35.

Example 20

4-{4-[(4-Benzyloxy-phenyl)-(3-methyl-but-2-enyl)-aminol]-piperidin-1-yl}-butan-2-ol was prepared in accordance with the methods of Example 1 (Steps 1–4), except that 3-hydroxybutyraldehyde was used instead of isovaleraldehyde in Step 4.

MS: 423 (M+1 for $C_{27}H_{38}N_2O_2$); an oil; TLC: $SiO_2$, $R_f$0.20 (9:1 EtOAc/MeOH);

Analysis ($C_{27}H_{38}N_2O_2$×0.25$H_2O$); (calc) C: 75.93, H: 9.10, N: 6.63, (found) C: 76.05, H: 9.08, N: 6.38.

Example 21

4-{4-[(4-Benzyloxy-phenyl)-(1-furan-2-ylmethyl-piperidin-4-yl)-(3-methyl-but-2-enyl)-amine was prepared in accordance with the methods of Example 1 (Steps 1–4), except that furan-2-carboxaldehyde was used instead of isovaleraldehyde in Step 4.

MS: 431 (M+1 for $C_{28}H_{34}N_2O_2$); an oil; TLC: $SiO_2$, $R_f$ 0.20 (1:1 hexanes/EtOAc);

Analysis ($C_{28}H_{34}N_2O_2$); (calc) C: 78.01, H: 7.90, N: 6.51, (found) C: 77.95, H:8.03, N: 6.43.

Example 22

(4-Benzyloxy-phenyl)-(3-methyl-but-2-enyl)-[1-(3-phenyl-propyl)-piperidin-4-yl]-amine was prepared in accordance with the methods of Example 1 (Steps 1–4), except that 3-phenylpropionaldehyde was used instead of isovaleraldehyde in Step 4.

MS: 469.3 (M+1 for $C_{32}H_{40}N_2O_1$); an oil; TLC: $SiO_2$, $R_f$ 0.32 (1:9 EtOAc/Hexane);

Analysis ($C_{32}H_{40}N_2O_1$); (calc) C: 82.01, H: 8.60, N: 5.98, (found) C: 82.02, H:8.36, N: 5.86.

Example 23

(4-Benzyloxy-phenyl)-(3-methyl-but-2-enyl)-(1-phenethyl-piperidin-4-yl)-amine was prepared in accordance with the methods of Example 1 (Steps 1–4), except that phenylacetaldehyde was used instead of isovaleraldehyde in Step 4.

MS: 455.2 (M+1 for $C_{31}H_{38}N_2O_1$); an oil; TLC: $SiO_2$, $R_f$ 0.40 (1:9 EtOAc/Hexane);

Analysis ($C_{31}H_{38}N_2O_1$); (calc) C: 81.90, H: 8.42, N: 6.16; (found) C: 81.87, H: 8.41, N: 5.91.

Example 24

(4-Benzyloxy-phenyl)-[1-(4-methanesulfinyl-benzyl)-piperidin-4-yl]-(3-methyl-but-2-enyl)-amine was prepared in accordance with the methods of Example 1 (Steps 1–4), except that 4-methylsulfonylbenzaldehyde was used instead of isovaleraldehyde in Step 4.

MS: 519.2 (M+1 for $C_{31}H_{38}N_2O_3S_1$); an oil; TLC: $SiO_2$, $R_f$ 0.24 (1:9 EtOAc/Hexane);

HPLC (C-18 column, 1:1 $CH_3CN/H_2O$+0.5% TFA): RT=3.62 min, 90% pure);

HRMS: (calc) 519.2681, (found) 519.2667.

Example 25

(4-Benzyloxy-phenyl)-[1-(4-fluoro-benzyl)-piperidin4-yl]-(3-methyl-but-2-enyl)-amine was prepared in accordance with the methods of Example 1 (Steps 1–4), except that 4-fluorobenzaldehyde was used instead of isovaleraldehyde in Step 4.

MS: 459.2 (M+1 for $C_{30}H_{35}N_2O_1F_1$); an oil; TLC: $SiO_2$, $R_f$ 0.32 (2:1 hexanes/EtOAc);

Analysis ($C_{30}H_{35}N_2O_1F_1$); (calc) C: 78.57, H: 7.69, N: 6.11, (found) C: 78.33, H: 7.67, N: 5.96.

Scheme VI

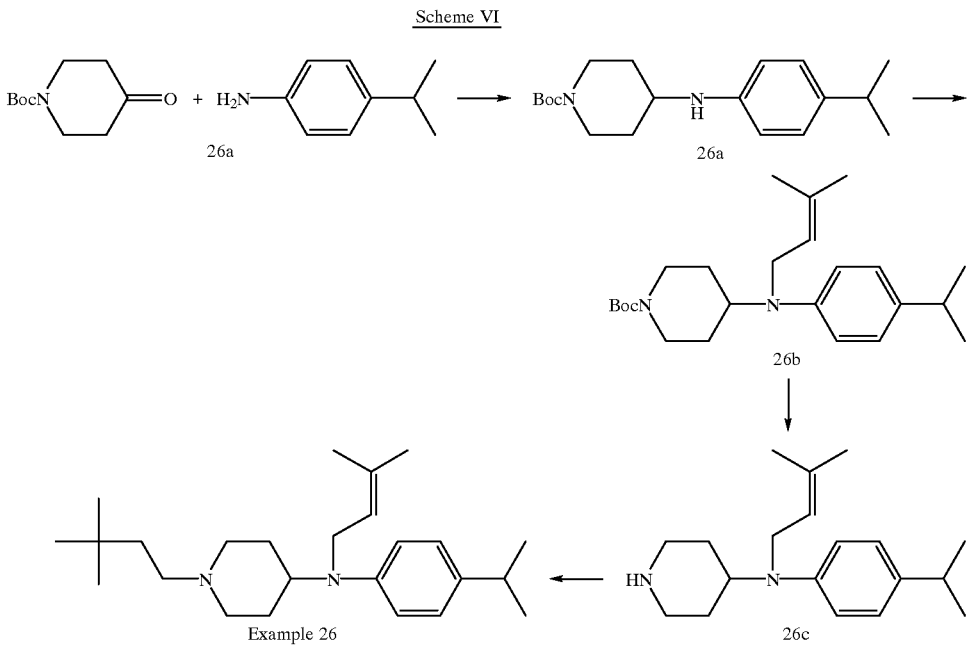

Example 26

[1-(3-Dimethyl-butyl)-piperidin-4yl]-(4-isopropyl-phenyl)-(3-methyl-but-2-enyl)-amine Step 1: 4-(4-Isopropyl-phenylamino)-piperidine-1-carboxylic acid tert-butyl ester (26a) was prepared in accordance with the methods of Step 1 in Example 1, except that 4-isopropylaniline was used instead of 4-Benzyloxyaniline hydrochloride salt.

MS: 319.3 (M+1 for $C_{19}H_{30}N_2O_2$); an oil; TLC: $SiO_2$, $R_f$ 0.57 (10% $MeOH/CH_2Cl_2$).

Step 2: 4-[(4-Isopropyl-phenyl)-(3-methyl-but-2-enyl)-amino]-piperidine-1-carboxylic acid tert-butyl ester (26b) was prepared in accordance with the methods of Step 2 in Example 1, except that 4-(4-Isopropyl-phenylamino)-piperidine-1-carboxylic acid tert-butyl ester (26a) was used instead of 4-(4-Benzyloxy-phenylamino)-piperidine-1-carboxylic acid tert-butyl ester (Ia).

MS: 387.3 (M+1 for $C_{24}H_{38}N_2O_2$); an oil; TLC: $SiO_2$, 0.33 (9:1 hexane/EtOAc).

Step 3: (4-Isopropyl-pbenyl)-(3-methyl-but-2-enyl)-piperidin-4-yl-amine (26c) was prepared in accordance with the methods of Step 3 in Example 1, except that 4-[(4-Isopropyl-phenyl)-(3-methyl-but-2-enyl)-amino]-piperidine-1-carboxylic acid tert-butyl ester (26b) was used instead of 4-[(4-Benzyloxy-phenyl)-(3-methyl-but-2-enyl)-amino]-piperidine-1-carboxylic acid tert-butyl ester (1b).

MS: 287.2 (M+1 for $C_{19}H_{30}N_2$); an oil; TLC: SiO2, $R_f$ 0.20 (10% MeOH/$CH_2Cl_2$).

Step 4: The preparation of Example 26: [1-(3,3-Dimethyl-butyl)-piperidin-4-yl]-(4-isopropyl-phenyl)-(3-methyl-but-2-enyl)-amine was prepared in accordance with the methods of Step 4 in Example 1, except that (4-Isopropyl-phenyl)-(3-methyl-but-2-enyl)-piperidin4-yl-amine (26c) was used instead of (4-Benzyloxy-phenyl-(3-methyl-but-2-enyl)-piperidin-4-yl-amine (1c) and 3,3-dimethylbutyraldehyde was used instead of isovaleraldehyde.

MS: 371.2 (M+1 for $C_{25}H_{32}N_2$); an oil; TLC: $SiO_2$, $R_f$ 0.45 (10% MeOH/$CH_2Cl_2$).

HPLC (C-18 column, 1:1 $CH_3CN/H_2O$+0.5% TFA): RT=4.317 min, 91% pure.

Example 27

4-{4[(4Isopropyl-phenyl)-(3-methyl-but-2-enyl)-amino]-piperidin-1-yl}-butan-2ol was prepared in accordance with the methods of Step 4 in Example 26, except that 3-hydroxybutyraldehyde was used instead of 3,3-dimethlbutyraldehyde.

MS: 359.2 (M+1 for $C_{23}H_{38}N_2O$); an oil; TLC: $SiO_2$, $R_f$ 0.47 (10% MeOH/$CH_2Cl_2$);

Analysis ($C_{23}H_{38}N_2O$); (calc) C: 77.04, H: 10.68, N: 7.81, (found) C: 77.40, H: 10.78 N: 7.80.

Example 28

(4-Isopropyl-phenyl)-(3-methyl-but-2-enyl)-[1-(3-methyl-butyl)-piperidin-4-yl]-amine was prepared in accordance with the methods of Step 4 in Example 26, except that isovaleraldehyde was used instead of 3,3-dimethylbutyraldehyde.

MS: 357.3 (M+1 for $C24H_{40}N_2$); an oil; TLC: $SiO_2$, $R_f$ 0.50 (10% MeOH/$CH_2Cl_2$);

HPLC (C-18 column, 1:1 $CH_3CN/H_2O$+0.5% TFA): RT=3.737 min, 92% pure.

Example 29

[1-(4-Fluoro-benzyl)-piperidin-4-yl]-(4-isopropyl-phenyl)-(3-methyl-but-2-enyl)-amine was prepared in accordance with the methods of Step 4 in Example 26, except that 4-fluorobenzaldehyde was used instead of 3,3-dimethylbutyraldehyde.

MS: 395.6 (M+1 for $C_{26}H_{35}N_2F$); an oil; TLC: $SiO_2$, $R_f$ 0.71 (10% MeOH/$CH_2Cl_2$);

Analysis ($C_{26}H_{35}N_2F$); (calc) C: 79.14, H: 8.94, N: 7.10, (found) C: 79.27, H: 8.86, N: 6.95.

HPLC (C-18 column, 1:1 $CH_3CN/H_2O$+0.5% TFA): RT=3.938 min, 97% pure.

Example 30

(4-Isopropyl-phenyl)-(3-methyl-but-2-enyl)-(1-pyridin-3-ylmethyl-piperidin-4-yl)-amine was prepared in accordance with the methods of Step 4 in Example 26, except that pyridine-3-carboxaldehyde was used instead of 3,3-dimethylbutyraldehyde.

MS: 378.2 (M+1 for $C_{25}H_{33}N_3$); an oil; TLC: $SiO_2$, $R_f$ 0.58 (10% MeOH/$CH_2Cl_2$);

HPLC (C-18 column, 1:1 $CH_3CN/H_2O$+0.5% TFA): RT=2.095 min, 99% pure.

Example 31

[1-(1H-Imidazol-4-ylmethyl)-piperidin-4-yl]-(4-isopropyl-phenyl)-(3-methyl-but-2-enyl)-amine was prepared in accordance with the methods of Step 4 in Example 26, except that imidazole4-carboxaldehyde was used instead of 3,3-dimethylbutyraldehyde.

MS: 367.2 (M+1 for $C_{23}H_{34}N_4$); an oil; TLC: $SiO_2$, $R_f$ 0.20 (5% MeOH/$CH_2Cl_2$);

HPLC (C-18 column, 1:1 $CH_3CN/H_2O$+0.5% TFA): RT=2.32 min, 85% pure.

Example 32

2-{4-[(4-lsopropyl-phenyl)-(3-methyl-but-2-enyl)-amino]-piperidin-1-yl}-propan-1-ol was prepared in accordance with the methods of Step 4 in Example 26, except that hydroxyacetone was used instead of 3,3-dimethylbutyraldehyde.

MS: 345.3 (M+1 for $C_{22}H_{36}N_2O_1$); an oil; TLC: $SiO_2$, $R_f$ 0.36 (6% MeOH/$CH_2Cl_2$);

Analysis ($C_{22}H_{36}N_2O_1 \times 0.4H_2O$); (calc) C: 75.12, H: 10.54, N: 7.96, (found) C: 75.32, H: 10.33, N: 7.64.

Example 33

(4-Isopropyl-phenyl)-(3-methyl-but-2-enyl)-[1-(1H-pyrrol-2-ylmethyl)-piperidin-4-yl]-amine was prepared in accordance with the methods of Step 4 in Example 26, except that pyrrole-2-carboxaldehyde was used instead of 3,3-dimethylbutyraldehyde.

MS: 366.2 (M+1 for $C_{24}H_{35}N_3$); an oil; TLC: $SiO_2$, $R_f$ 0.18 (4% MeOH/$CH_2Cl_2$);

Analysis ($C_{24}H_{35}N_3 \times 0.25H_2O$); (calc) C: 77.90, H: 9.67, N: 11.35, (found) C: 77.91, H: 9.66, N: 11.37.

Example 34

(4-Isopropoxy-phenyl)-(3-methyl-but-2-enyl)-[1-(3-methyl-butyl)-piperidin-4-yl]-amine Step 1: 4-(4-lsopropoxy-phenylamino)-piperidine-1-carboxylic acid tert-butyl ester (34a) was prepared in accordance with the methods of Step 1 in Example 1, except that 4-isopropoxyaniline was used instead of 4-Benzyloxyaniline hydrochloride salt.

MS: 335.3 (M+1 for $C_{19}H_{30}N_2O_3$); an oil; TLC: $SiO_2$, $R_f$ 0.74 (1:1 hexanes/EtOAc).

Step 2: 4-[(4-Isopropoxy-phenyl)-(3-methyl-but-2-enyl)-amino]-piperidine-1-carboxylic acid tert-butyl ester (34b) was prepared in accordance with the methods of Step 2 in Example 1, except that 4-(4-Isopropoxy-phenylamino)-piperidine-1-carboxylic acid tert-butyl ester (34a) was used instead of 4-(4-Benzyloxy-phenylamino)-piperidine-1-carboxylic acid tert-butyl ester (1a).

MS: 403.3 (M+1 for $C_{24}H_{38}N_2O_3$); an oil; TLC: $SiO_2$, $R_f$ 0.50 (3:1 hexanes/EtOAc).

Step 3: (4-Isopropoxy-phenyl)-(3-methyl-but-2-enyl)-piperidin-4-yl-amine (34c) was prepared in accordance with the methods of Step 3 in Example 1, except that 4-(4-Isopropoxy-phenyl)-(3-methyl-but-2-enyl)-amino]- piperidine-1-carboxylic acid tert-butyl ester (34b) was used instead of 4-[(4-Benzyloxy-phenyl)-(3-methyl-but-2-enyl)-amino]-piperidine-1-carboxylic acid tert-butyl ester (1b).

MS: 303.3 (M+1 for $C_{19}H_{30}N_2O$); an oil; TLC: $SiO_2$, $R_f$0.24 (8% MeOH/$CH_2Cl_2$).

Step 4: The preparation of Example 26: (4-Isopropoxy-phenyl)-(3-methyl-but-2-enyl)-[1-(3-methyl-butyl)-piperidin-4-yl]-amine was prepared in accordance with the methods of Step 4 in Example 1, except that (4-Isopropoxy-phenyl)-(3-methyl-but-2-enyl)-piperidin-4-yl-amine (34c) was used instead of (4-Benzyloxy-phenyl)-(3-methyl-but-2-enyl)-piperidin-4-yl-amine (1c).

accordance with the methods of Step 4 in Example 34, except that 3,3-dimethylbutylaldehyde was used instead of isovaleraldehyde.

MS: 387 (M+1 for $C_{25}H_{42}N_2O$); an oil; TLC: $SiO_2$, $R_f$0.2 (2:1 hexanes/EtOAc);

Analysis ($C_{25}H_{42}N_2O$); (calc) C: 77.67, H: 10.95, N: 7.25, (found) C: 77.34, H: 10.84, N, 7.20.

Scheme VII

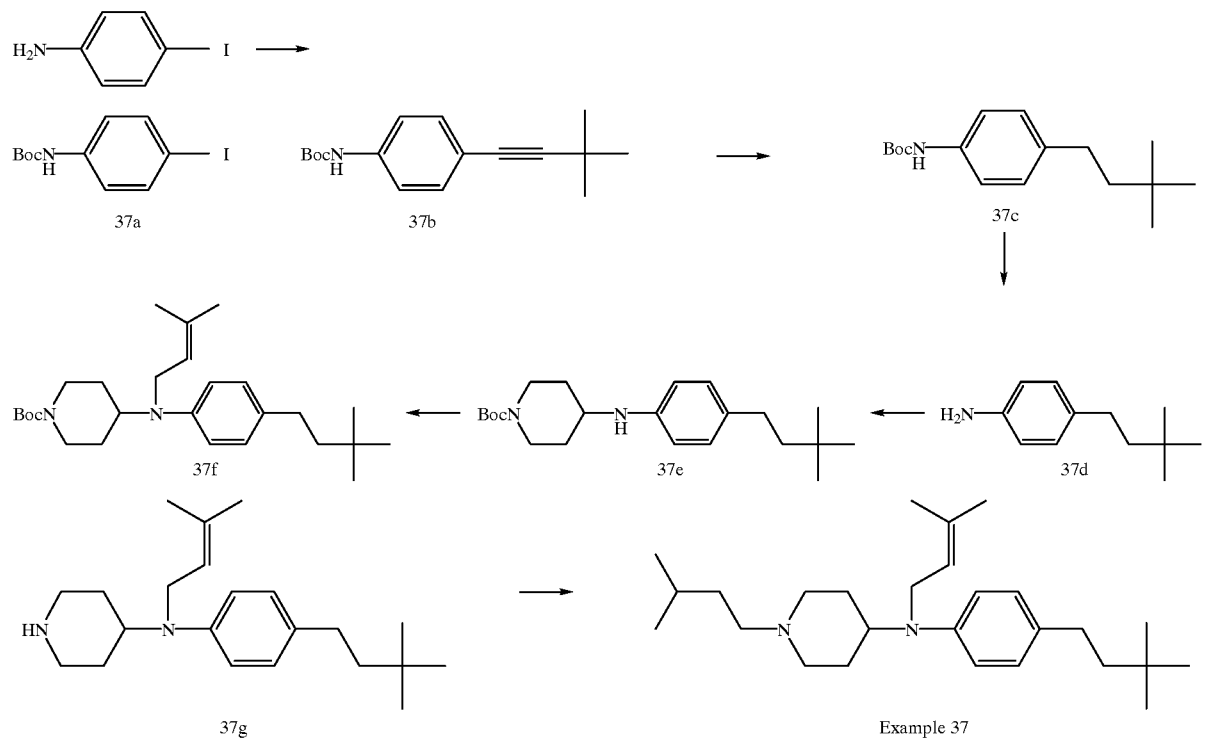

MS: 373.2 (M+1 for $C_{24}H_{40}N_2O$); an oil; TLC: $SiO_2$, $R_f$0.5 (10% MeOH/$CH_2Cl_2$);

HPLC (C-18 column, 1:1 $CH_3CN/H_2O$+0.5% TFA): RT=3.400 min, 100% pure.

Analysis ($C_{24}H_{40}N_2O×0.35H_2O$); (calc) C: 76.08, H: 10.83, N: 7.39, (found) C: 76.15, H: 10.84, N, 7.25.

Example 35

[1-(4-Fluoro-benzyl)-piperidin-4-yl]-(4-isopropoxy-phenyl)-(3-methyl-but-2-enyl)-amine was prepared in accordance with the methods of Step 4 in Example 34, except that 4-fluorobenzaldehyde was used instead of isovaleraldehyde.

MS: 411.2 (M+1 for $C_{26}H_{35}N_2O_1F_1$); an oil; TLC: $SiO_2$, $R_f$0.58 (10% MeOH/$CH_2Cl_2$);

HPLC (C-18 column, 1:1 $CH_3CN/H_2O$+0.5% TFA): RT=3.488 min, 95% pure.

Example 36

[1-(3,3-Dimethyl-butyl)-piperidin-4-yl-(4-isopropoxy-phenyl)-(3-methyl-but-2-enyl)-amine was prepared in Example 37

[4-(3,3-Dimethyl-butyl)-phenyl]-(3-methyl-but-2-enyl)-[1-(3-methyl-butyl)-piperidin-4-yl]-amine Step 1: Preparation of (4-Iodo-phenyl)-carbamic acid tert-butyl ester (37a): 4-iodoaniline (10.0 g, 45.6 mmol) was dissolved in THF (50 mL) in an amber flask, cooled to 0° C., and treated with tert-butoxycarbonyl anhydride. The reaction was heated to 60° C. overnight, then concentrated in vacuo to give 15.5 g (106%) of the crude product which was used without further purification.

MS: 318.0 (M−1 for $C_{11}H_{14}N_1O_2I_1$ in APCI⁻ spectrum); TLC: $SiO_2$, $R_f$0.42 (6:1 hexanes/EtOAc).

Step 2: Preparation of [4-(3,3-Dimethyl-but-1-ynyl)-phenyl]-carbamic acid tert-butyl ester (37b): (4-Iodo-phenyl)-carbamic acid tert-butyl ester (37a, 1.0 g, 3.13 g) was dissolved in THF (30 mL) and treated with $Et_3N$ (2.2 mL, 15.7 mmol), 3,3-dimethyl- 1-butyne (0.58 mL, 4.70 mmol), bis(triphenylphosphine) palladium (II) chloride (0.218 g, 0.31 mmol), and copper (I) iodide (0.03 g, 0.16 mmol). The reaction was stirred overnight at room temperature, then filtered and concentrated. The residue was chromatographed on silica gel eluting with 8:1 hexanes/ EtOAc to give 0.7 g (82%) of the mostly clean desired product which was carried on without further purification.

MS: 272.0 (M−1 for $C_{17}H_{23}N_1O_2$ in APCI⁻ spectrum); TLC: $SiO_2$, $R_f$0.42 (6:1 hexanes/EtOAc).

Step 3: Preparation of [4-(3,3-Dimethyl-butyl)-phenyl]-carbamic acid tert-butyl ester (37c): [4-(3,3-Dimethyl-but-1-ynyl)-phenyl]-carbamic acid tert-butyl ester (37b, 2.50 g, 9.15 mmol) was treated with 1:1 THF/MeOH (50 mL) and Pd/C (0.5 g, 10%), shaken for 15.8 hours under an atmosphere of $H_2$ (51.4 psi). More Pd/C (0.5 g, 20%) was added and the reaction was stirred for an additional 1.13 hours, then filtered and concentrated. The crude material was chromatographed on silica gel eluting with 1:9 EtOAc/Hexane to give 2.39 g (94%) of the desired product.

MS: 276.2 (M−1 for $C_{17}H_{27}NO_2$ in APCI- spectrum); an oil; TLC: $SiO_2$, $R_f$0.95 (10% MeOH/$CH_2Cl_2$).

Step 4: Preparation of 4-(3,3-Dimethyl-butyl)-phenylamine (37d): [4-(3,3-Dimethyl-butyl)-phenyl]-carbamic acid tert-butyl ester (37c, 2.39 g, 8.60 mmol) was dissolved in $CH_2Cl_2$ (30 mL) and treated with TFA (30 mL) and stirred for 30 minutes. The solution was concentrated down and pumped under high vacuum for 10 minutes. The reaction was diluted with EtOAc (500 mL), washed three times with saturated bicarbonate solution and once with brine, dried over $Na_2SO_4$, and carried on to Step 5 (assuming 100% yield) without further purification.

TLC: $SiO_2$, $R_f$0.70 (10% MeOH/$CH_2Cl_2$).

Step 5: 4-[4-(3,3-Dimethyl-butyl)-phenylamino]-piperidine-1-carboxylic acid tert-butyl ester (37e) was prepared in accordance with the methods of Step 1 in Example 1, except that 4-(3,3-Dimethyl-butyl)-phenylamine (37d) was used instead of 4-Benzyloxyaniline hydrochloride salt.

MS: 361.3 (M+1 for $C_{22}H_{36}N_2O_2$); an oil; TLC: SiO2 $R_f$0.48 (3% MeOH/$CH_2Cl_2$).

Step 6: 4-[[4-(3,3-Dimethyl-butyl)-phenyl]-(3-methyl-but-2-enyl)-amino]-piperidine-1-carboxylic acid tert-butyl ester (37f) was prepared in accordance with the methods of Step 2 in Example 1, except that 4-[4-(3,3-Dimethyl-butyl)-phenylamino]-piperidine-1-carboxylic acid tert-butyl ester (37e) was used instead of 4-(4-Benzyloxy-phenylamino)-piperidine-1-carboxylic acid tert-butyl ester (Ia).

MS: 429.4 (M+1 for $C_{27}H_{44}N_2O_2$); an oil; TLC: $SiO_2$, $R_f$0.23 (9:1 hexane/EtOAc).

Step 7: [4-(3,3-Dimethyl-butyl)-phenyl]-(3-methyl-but-2-enyl)-piperidin4-yl-amine (37g) was prepared in accordance with the methods of Step 3 in Example 1, except that 4-[[4-(3,3-Dimethyl-butyl)-phenyl]-(3-methyl-but-2-enyl)-amino]-piperidine-1-carboxylic acid tert-butyl ester (37f) was used instead of 4[-(-4-Benzyloxy-phenyl)-(3-methyl-but-2-enyl)-amino]-piperidine-1-carboxylic acid tert-butyl ester (Ib).

MS: 329.2 (M+1 for $C_{22}H_{36}N_2$); an oil; TLC: $SiO_2$, $R_f$0.14 (10% MeOH/$CH_2Cl_2$).

Step 8: The preparation of Example 37: [4-(3,3-Dimethyl-butyl)-phenyl]-(3-methyl-but-2-enyl)-[1-(3-methyl-butyl)-piperidin-4-yl]-amine was prepared in accordane with the methods of Step 4 in Example 1, except that [4-(3,3-Dimethyl-butyl)-phenyl]-(3-methyl-but-2-enyl)-piperidin-4-yl-amine (37g) was used instead of (4-Benzyloxy-phenyl)-(3-methyl-but-2-enyl)-piperidin-4-yl-amine (Ic).

MS: 399.3 (M+1 for $C_{27}H_{46}N_2$); an oil; TLC: $SiO_2$, $R_f$0.26 (5% MeOH/$CH_2Cl_2$);

Anaylsis ($C_{27}H_{46}N_2$); (calc) C: 81.34, H: 11.63, N: 7.03, (found) C: 81.23, H: 11.49,N: 6.98.

Example 38

[4-(3,3-Dimethyl-butyl)-phenyl]-[1-(3,3-dimethyl-butyl)-piperidin-4-yl]-(3-methyl-but-2-enyl)-amine was prepared in accordance with the methods of Step 8 in Example 37, except that 3,3-dimethylbutyraldehyde was used instead of isovaleraldehyde. The final compound was converted to the HCl salt.

MS: 413 (M+1 for $C_{28}H_{48}N_2$); mp 195° C. (dec.);

HRMS: (calc) 413.3896 (found) 413.3895.

Example 39

[1-(4-Dimethylamino-benzyl)-piperidin-4-yl]-[4-(3,3-dimethyl-butyl)-phenyl]-(3-methyl-but-2-enyl)-amine was prepared in accordance with the methods of Step 8 in Example 37, except that 4-dimethylaminobenzaldehyde was used instead of isovaleraldehyde.

MS: 462.4 (M+1 for $C_{31}H_{47}N_3$); an oil; TLC: $SiO_2$, $R_f$0.27 (6% MeOH/$CH_2Cl_2$);

HPLC (C-18 column, 1:1 $CH_3CN/H_2O$+0.5% TFA): RT=3.612 min, 100% pure.

Scheme VIII

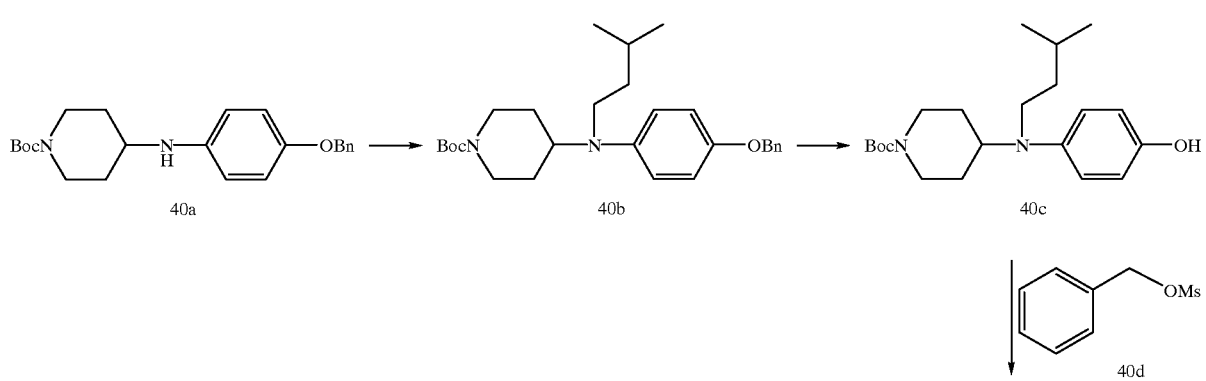

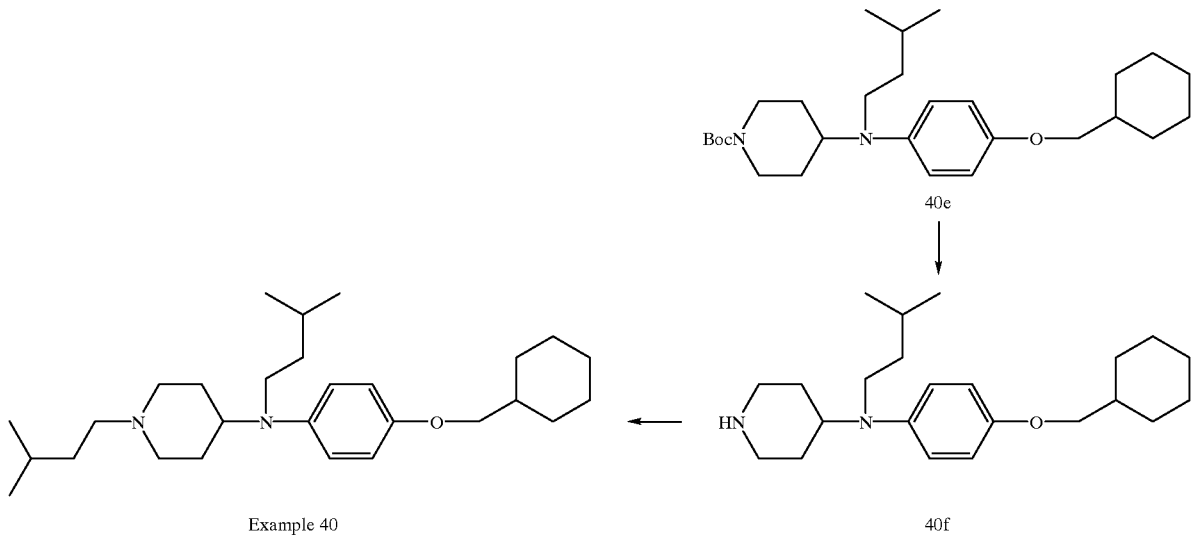

Example 40
4f

Example 40

(4-Cyclohexylmethoxy-phenyl)-(3-methyl-butyl)-[1-(3-methyl-butyl)-piperidin-4-yl]-amine Step 1: 4-(4-Benzyloxy-phenylamnino)-piperidine-1-carboxylic acid tert-butyl ester (40a) was prepared according to Step 1 in Example 1.

Step 2: Preparation of 4-[(4-Benzyloxy-phenyl)-(3-methyl-butyl)-amino]-piperidine-1-carboxylic acid tert-butyl ester (40b): 4-(4-Benzyloxy-phenylamino)-piperidine-1-carboxylic acid tert-butyl ester (40a, 3.0 g, 7.84 mmol) was dissolved in $CH_2Cl_2$ (50 mL) and treated with isovaleraldehyde (0.84 mL, 7.84 mmol). The reaction was stirred for 30 minutes, then cooled to 0° C., treated with NaBH(OAc)$_3$, and stirred overnight. The reaction was diluted with EtOAc (400 mL), washed with saturated bicarbonate solution and brine, dried over $Na_2SO_4$, and concentrated. The residue was chromatographed on silica gel eluting with 6% MeOH/$CH_2Cl_2$ to give 3.3 g (93%) of the desired product.

MS: 453.3 (M+1 for $C_{28}H_{40}N_2O_3$); an oil; TLC: $SiO_2$, $R_f$ 0.34 (6% MeOH/$CH_2Cl_2$);

Analysis ($C_{28}H_{40}N_2O_3$); (calc) C: 74.30, H: 8.91, N: 6.19, (found) C: 74.34, H: 9.08, N: 6.04.

Step 3: Preparation of 4-[(4-Hydroxy-phenyl)-(3-methyl-butyl)-amino]-piperidine-1-carboxylic acid tert-butyl ester (40c): 4-[(4-Benzyloxy-phenyl)-(3-methyl-butyl)-amino]-piperidine-1-carboxylic acid tert-butyl ester (40b, 14.53 g, 32.10 mmol) was treated with 1:1 THF/MeOH (200 mL) and Pd/C (1.5 g, 20%). Shaken for 14 hours under an atmosphere of $H_2$ (49.7 psi), filtered, and concentrated to give 13.80 g (119%) of the crude product which was used without further purification.

MS: 363.2 (M+1 for $C_{21}H_{34}N_2O_3$); sticky solid; TLC: $SiO_2$, $R_f$ 0.61 (10% MeOH/$CH_2Cl_2$);

Analysis ($C_{21}H_{34}N_2O_3 \times 0.35 H_2O$); (calc) C: 68.39, H: 9.48, N: 7.60, (found) C: 68.60, H: 9.83, N: 7.33.

Step 4a: Preparation of Methanesulfonic acid cyclohexylmethyl ester (40d): Cyclohexylmethanol (1.25 mL, 10.0 mmol) was dissolved in $CH_2Cl_2$ (50 mL), treated with diisopropylethylamine (7.0 mL, 40.0 mmol), cooled to 0° C., treated with methanesulfonyl chloride (0.85 mL, 11.0 mmol), and stirred for 1 hour at room temperature. The reaction was diluted with $CH_2Cl_2$ (200 mL), washed with saturated bicarbonate solution and brine, dried over $Na_2SO_4$, and concentrated to give 2.42 g (125% crude yield) of the desired product which was used immediately without purification.

$^1$H NMR (CDCl$_3$) δ 0.91–1.75 (m, 11 H), 2.96 (s, 3 H), 3.98 (d, 2 H, J=6.3 Hz).

Step 4b: Preparation of 4-[(4-Cyclohexylmethoxy-phenyl)-(3-methyl-butyl)-amnino]-piperidine-1-carboxylic acid tert-butyl ester (40e): 4-[(4-Hydroxy-phenyl)-(3-methyl-butyl)-amino]-piperidine-1-carboxylic acid tert-butyl ester (40c, 1.01 g, 2.77 mmol) was dissolved in DMF (28 mL), cooled to 0° C., treated with NaH (0.22 g, 60% dispersion in mineral oil, 5.54 mmol), stirred 10 minutes, treated with Methanesulfonic acid cyclohexylmethyl ester (40d, 0.222 g, 5.54 mmol) and heated to 50° C. for 2 hours. The reaction was treated further with NaH (0.11 g, 2.77 mmol) and heated to 50° C. overnight. The reaction was diluted with EtOAc (200 mL), washed with saturated bicarbonate solution and brine, dried over $Na_2SO_4$, and concentrated. The residue was chromatographed on silica gel eluting with 5:1 hexane/EtOAc to give 1.08 g (85%) of the desired product.

MS: 459.4 (M+1 for $C_{28}H_{46}N_2O_3$); an oil; TLC: $SiO_2$, $R_f$ 0.64 (3:1 hexane/EtOAc);

Analysis ($C_{28}H_{46}N_2O_3$); (calc) C: 73.32, H: 10.11, N: 6.11, (found) C: 73.64, H: 9.80, N: 6.01.

Step 5: Preparation of (4-Cyclohexylmethoxy-phenyl)-(3-methyl-butyl)-piperidin-4-yl-amine (40f): 4-[(4-Cyclohexylmethoxy-phenyl)-(3-methyl-butyl)-amino]-piperidine-1-carboxylic acid tert-butyl ester (40e, 1.08 g, 2.36 mmol) was dissolved in $CH_2Cl_2$ (8 mL), treated with TFA (8 mL), and stirred for 30 minutes. The reaction was concentrated in vacuo, diluted with EtOAc (200 mL), washed three times with saturated bicarbonate solution and once with brine, dried over $Na_2SO_4$, and concentrated to give 0.78 (92%) of the desired product which was used without further purification.

MS: 359.2 (M+1 for $C_{23}H_{38}N_2O_1$); an oil; TLC: $SiO_2$, $R_f$ 0.21 (10% MeOH/$CH_2Cl_2$);

HPLC (C-18 column, 1:1 $CH_3CN/H_2O$+0.5% TFA): RT=5.45 min, 100% pure.

Step 6: The preparation of Example 40: (4-Cyclohexylmethoxy-phenyl)-(3-methyl-butyl)-[1-(3-methyl-butyl)-piperidin-4-yl]-amine:

(4-Cyclohexylmethoxy-phenyl)-(3-methyl-butyl)-piperidin-4-yl-amine (40f, 0.20 g, 0.56 mmol) was dissolved in $CH_2Cl_2$ (4 mL), treated with isovaleraldehyde (61 µL, 0.56 mmol), stirred for 30 minutes, cooled to 0° C., treated with $NaBH(OAc)_3$ (0.177 g, 0.84 mmol) and stirred overnight at room temperature. The reaction was diluted with EtOAc (100 mL), washed with saturated bicarbonate solution and brine, dried over $Na_2SO_4$, and concentrated. The residue was chromatographed on silica gel eluting with 4% MeOH/$CH_2Cl_2$ to give 201 mg (84%) of the desired product.

MS: 429.3 (M+1 for $C_{28}H_{48}N_2O_1$); an oil; TLC: $SiO_2$, $R_f$0.26 (6% MeOH/$CH_2Cl_2$);

Analysis ($C_{28}H_{46}N_2O_3 \times 0.2H_2O$); (calc) C: 77.79, H: 11.28, N: 6.48, (found) C: 77.93, H: 11.11, N: 6.31.

Example 41

4-{4-[(4-Cyclohexylmethoxy-phenyl)-(3-methyl-butyl)-amino]-piperidin-1-yl}-butan-2-ol was prepared in accordance with the methods of Step 7 in Example 40, except that 3-hydroxybutyraldehyde was used instead of isovaleraldehyde.

MS: 431.4 (M+1 for $C_{27}H_{46}N_2O_2$); an oil; TLC: $SiO_2$, $R_f$0.30 (7% MeOH/$CH_2Cl_2$);

Analysis ($C_{27}H_{46}N_2O_2$); (calc) C: 75.30, H: 10.77, N: 6.50, (found) C: 75.31, H: 10.44, N: 6.33.

Example 42

(4-Cyclohexylmethoxy-phenyl)-[1-(3,3-dimethyl-butyl)-piperidin-4-yl]-(3-methyl-butyl)-amine was prepared in accordance with the methods of Step 7 in Example 40, except that 3,3-dimethylbutyaldehyde was used instead of isovaleraldehyde.

MS: 443 (M+1 for $C_{28}H_{50}N_2O_1$); sticky solid; TLC: $SiO_2$, $R_f$0.40 (2:1 hexane/EtOAc);

Analysis ($C_{28}H_{50}N_2O_1$); (calc) C: 78.68, H: 11.38, N: 6.33, (found) C: 78.62, H: 11.21, N:6.24.

Example 43

Step 1: Methanesulfonic acid 4-fluoro-benzyl ester (43a) was prepared in accordance with the methods of Step 4 in Example 40, except that 4-fluorobenzyl alcohol was used instead of cyclohexylmethanol.

MS: 205.2 (M+1 for $C_8H_9F_1O_3S_1$); sticky solid; TLC: $SiO_2$, $R_f$0.41 (2:1 hexane/EtOAc).

Step 2: 4-[[4-(4-Fluoro-benzyloxy)-phenyl]-(3-methyl-butyl)-amino]-piperidine-1-carboxylic acid tert-butyl ester (43b) was prepared in accordance with the methods of Step 5 in Example 40, except that Methanesulfonic acid 4-fluoro-benzyl ester (43a) was used instead of Methanesulfonic acid cyclohexylmethyl ester (40d).

MS: 471.2 (M+1 for $C_{28}H_{39}N_2O_3F_1$); an oil; TLC: $SiO_2$, $R_f$0.35 (4:1 hexane/EtOAc);

Analysis ($C_{28}H_{39}N_2O_3F_1$); (calc) C: 71.46, H: 8.35, N: 5.95, (found) C: 71.37, H: 8.09, N: 5.73.

Step 3: [4-(4-Fluoro-benzyloxy)-phenyl]-(3-methyl-butyl)-piperidin-4-yl-amine (43c) was prepared in accordance with the methods of Step 6 in Example 40, except that 4-[[4-(4-Fluoro-benzyloxy)-phenyl]-(3-methyl-butyl)-amino]-piperidine-1-carboxylic acid tert-butyl ester (43b) was used instead of 4-[(4-Cyclohexylmethoxy-phenyl)-(3-methyl-butyl)-amino]-piperidine-1-carboxylic acid tert-butyl ester (40e).

MS: 371.2 (M+1 for $C_{23}H_{31}N_2O_1F_1$); an oil; TLC: $SiO_2$, $R_f$0.41 (10% MeOH/$CH_2Cl_2$);

Analysis ($C_{23}H_{31}N_2O_1F_1 \times 0.8H_2O \times 0.5$ TFA); (calc) C: 65.23, H: 7.55, N: 6.34, (found) C: 65.25, H: 7.57, N: 6.22.

Step 4: The preparation of Example 43: [1-(3,3-Dimethyl-butyl)-piperidin-4-yl]-[4-(4-fluoro-benzyloxy)-phenyl]-(3-methyl-butyl)-amine was prepared in accordance with the methods of Step 7 in Example 40, except that [4-(4-Fluoro-benzyloxy)-phenyl]-(3-methyl-butyl)-piperidin-4-yl-amine (43c) was used instead of (4-Cyclohexylmethoxy-phenyl)-(3-methyl-butyl)-piperidin-4-yl-amine (40f) and 3,3-dimethylbutyraldehyde was used instead of isovaleraldehyde.

MS: 456 (M+1 for $C_{29}H_{43}N_2O_1F_1$); sticky solid; TLC: $SiO_2$, $R_f$0.35 (1:1 hexanes/EtOAc);

Analysis ($C_{29}H_{43}N_2O_1F_1$); (calc) C: 76.61, H: 9.53, N: 6.16, (found) C: 76.78, H: 9.28, N: 6.15.

Example 44

(S)-1-{4-[(4-Benzyloxy-phenyl)-(3-methyl-but-2-enyl)-amino]-piperidin-1-yl}-2-hydroxy-4-methyl-pentan-1-one: (4-Benzyloxy-phenyl)-(3-methyl-but-2-enyl)-piperidin-4-yl-amine (Ic) (0.89 g, 2.54 mmol) was dissolved in DMF (17 mL) and treated with N,N-diisopropyletbylamine (1.77 mL, 10.17 mmol), L-2-hydroxyisocaproic acid (0.34 g, 2.54 mmol), and HBTU (0.96 g, 2.54 mmol). The reaction was stirred for 3 hours, then diluted with EtOAc (200 mL), washed with saturated bicarbonate solution and brine, dried over $Na_2SO_4$, and concentrated. The residue was chromatographed on silica gel eluting with 4% MeOH/$CH_2Cl_2$ to give 0.58 g (49%) of the desired product.

MS: 465.2 (M+1 for $C_{29}H_{40}N_2O_3$); an oil; TLC: $SiO_2$, $R_f$0.47 (5% MeOH/$CH_2Cl_2$);

Analysis ($C_{29}H_{40}N_2O_3$); (calc) C: 74.96, H: 8.68, N: 6.03, (found) C: 74.59, H: 8.65, N: 5.87.

Example 45

(S)-2-Hydroxy-1-{4-[(4-isopropyl-phenyl)-(3-methyl-but-2-enyl)-arnino]-piperidin-1-yl}-4-methyl-pentan-1-one was made in accordance with the methods of Example 44 except that (4-Isopropyl-phenyl)-(3-methyl-but-2-enyl)-piperidin-4-yl-amine (26c) was used instead of Ic (4-Benzyloxy-phenyl)-(3-methyl-but-2-enyl)-piperidin-4-yl-amine.

MS: 401.3 (M+1 for $C_{25}H_{40}N_2O_2$); an oil; TLC: $SiO_2$, $R_f$0.27 (3:1 hexane/EtOAc);

Anaylsis ($C_{25}H_{40}N_2O_2$); (calc) C: 74.96, H: 10.06, N: 6.99, (found) C: 74.77, H: 9.70, N: 6.87.

Example 46

The preparation of (3-Benzyloxy-phenyl)-[1-(3,3-dimethyl-butyl)-piperidin-4-yl]-(3-methyl-but-2-enyl)-amine Step 1: 4-(3-Benzyloxy-phenylamino)-piperidine-1-carboxylic acid tert-butyl ester (46a): was prepared in accordance with the methods of Step 1 in Example 1, except that 3-benzyloxyaniline was used instead of 4-benzyloxyaniline hydrohoride salt.

MS: 383.2 (M+1 for $C_{23}H_{30}N_2O_3$); an oil; TLC: $SiO_2$, $R_f$0.8 (10% MeOH/$CH_2Cl_2$).

Step 2: 4-[(3-Benzyloxy-phenyl)-(3-methyl-but-2-enyl)-amino]-piperidine-1-carboxylic acid tert-butyl ester (46b) was prepared in accordance with the methods of Step 2 in Example 1, except that 4-(3-Benzyloxy-phenylamino)-pipendine-1-carboxylic acid tert-butyl ester (46a) was used instead of 4-(4-Benzyloxy-phenylarnino)-piperidine-1-carboxylic acid tert-butyl ester (Ia).

MS: 451.3 (M+1 for $C_{28}H_{38}N_2O_3$); an oil; TLC: $SiO_2$, $R_f$0.37 (10:1 Hexane/EtOAc).

Step 3: (3-Benzyloxy-phenyl)-(3-methyl-but-2-enyl)-piperidin-4-yl-amine (46c) was prepared in accordance with the methods of Step 3 in Example 1, except that 4-[(3-Benzyloxy-phenyl)(3-methyl-but-2-enyl)-amino]-piperidine-1-carboxylic acid tert-butyl ester (46b) was used instead of 4-[(4-Benzyloxy-phenyl)-(3-methyl-but-2-enyl)-amino]-piperidine-1-carboxylic acid tert-butyl ester (Ib).

MS: 351.2 (M+1 for $C_{23}H_{30}N_2O$); sticky solid; TLC: $SiO_2$, $R_f$0.25 (10% $MeOH/CH_2Cl_2$).

Step 4: The preparation of Example 46: (3-Benzyloxy-phenyl)-[1-(3,3-dimethyl-butyl)-piperidin-4-yl]-(3-methyl-but-2-enyl)-amine was prepared in accordance with the methods of Step 4 in Example 1 except that (3-Benzyloxy-phenyl)-(3methyl-but-2-enyl)-piperidin4yl-amine (46c) was used instead of (4-Benzyloxy-phenyl)-(3-methyl-but-2-enyl)-piperidin-4-yl-amine (Ic).

MS: 435 (M+1 for $C_{29}H_{42}N_2O_1$); sticky solid; TLC: $SiO_2$, $R_f$0.70 (1:1 hexanes/EtOAc);

Analysis ($C_{29}H_{42}N_2O_1$); (calc) C: 80.13, H: 9.74, N: 6.44, (found) C: 79.88, H:9.04, N: 6.39.

Example 47

[4-(3,3-Dimethyl-butyl)-phenyl]-(3-methyl-but-2-enyl)-[1-(1H-pyrrol-2-ylmethyl)-piperidin-4-yl]-amine was prepared in accordance with the methods of Steps 1–8 in Example 37 except that pyrrole-2-carboxaldehyde was used instead of isovaleraldehyde in Step 8. The compound was further prepared as the HCl salt.

MS: 408 (M+1 for $C_{27}H_{41}N_3$); mp 317–319° C.

Example 48

[1-(3 3-Dimethyl-butyl)-piperidin-4-yl]-(3-methyl-but-2-enyl)-(4-phenethyl-phenyl)-amine Step 1: (4-Iodo-phenyl)-carbamic acid tert-butyl ester (48a) was prepared in accordance with the methods of Step 1 in Example 37.

Step 2: (4-Phenylethynyl-phenyl)-carbamic acid tert-butyl ester (48b) was prepared in accordance with the methods of Step 2 in Example 37 except that phenylacetylene was used instead of 3,3-dimethyl-1-butyne.

MS: 292.1 (M–1 for $C_{19}H_{19}N_1O_2$ in APCI⁻ spectrum); TLC: $SiO_2$, $R_f$0.24 (6:1 hexane/EtOAc)

Step 3: (4-Phenethyl-phenyl)-carbamic acid tert-butyl ester (48c) was prepared in accordance with the methods of Step 3 in Example 37 except that (4-Phenylethynyl-phenyl)-carbamic acid tert-butyl ester (48b) was used instead of [4-(3,3-Dimethyl-but-1-ynyl)-phenyl]-carbamic acid tert-butyl ester (37b).

MS: 296.1 (M–1 for $C_{19}H_{23}N_1O_2$ in APCI⁻ spectrum); TLC: $SiO_2$, $R_f$0.34 (6:1 hexane/EtOAc).

Step 4: 4-Phenethyl-phenylamine (48d) was prepared in accordance with the methods of Step 4 in Example 37 except that (4-Phenethyl-phenyl)-carbamic acid tert-butyl ester (48c) was used instead of [4-(3,3-Dimethyl-butyl)-phenyl]-carbamic acid tert-butyl ester (37c).

MS: 239.2 (M+1 for $C_{14}H_{15}N_1 \times CH_3CN$); TLC: $SiO_2$, $R_f$0.47 (10% $MeOH/CH_2Cl_2$).

Step 5: 4-(4-Phenethyl-phenylamino)-piperidine-1-carboxylic acid tert-butyl ester (48e) was prepared in accordance with the methods of Step 5 in Example 37 except that 4-Phenethyl-phenylamine (48d) was used instead of 4-(3,3-Dimethyl-butyl)-phenylamine (37d). The mass spectrum of the crude product showed both the expected peak (381.1) and incompletely reduced alkene (379.1). The crude mixture was dissolved in MeOH (75 mL), treated with Raney nickel (1.0 g), and shaken for 1 hour under an atmosphere of $H_2$ (50 psi). The reaction was filtered, concentrated, and carried on without further purification.

MS: 381.1 (M+1 for $C_{24}H_{32}N_2O_2$); TLC: $SiO_2$, $R_f$0.79 (2:1 hexane/EtOAc).

Step 6: 4-[(3-Methyl-but-2-enyl)-(4-phenethyl-phenyl)-amino]-piperidine-1-carboxylic acid tert-butyl ester (48f) was prepared in accordance with the methods of Step 6 in Example 37 except that 4-(4-Phenethyl-phenylamino)-piperidine-1-carboxylic acid tert-butyl ester (48e) was used instead of 4-[4-(3,3-Dimethyl-butyl)-phenylamino]-piperidine-1-carboxylic acid tert-butyl ester (37e).

MS: 449.3 (M+1 for $C_{29}H_{40}N_2O_2$); an oil; TLC: $SiO_2$, $R_f$0.53 (5:1 hexane/EtOAc);

Analysis ($C_{29}H_{40}N_2O_2$); (calc) C: 77.17, H: 9.00, N: 6.21, (found) C: 77.19, H: 9.00, N: 6.17.

Step 7: (3-Methyl-but-2-enyl)-(4-phenethyl-phenyl)-piperidin-4-yl-amine (48g) was prepared in accordance with the methods of Step 7 in Example 37 except that 4-[(3-Methyl-but-2-enyl)-(4-phenethyl-phenyl)-amino]-piperidine-1-carboxylic acid tert-butyl ester (48f) was used instead of 4-[[4-(3,3-Dimethyl-butyl)-phenyl]-(3-methyl-but-2-enyl)-amino]-piperidine-1-carboxylic acid tert-butyl ester (37f).

MS: 349.2 (M+1 for $C_{24}H_{32}N_2$); an oil; TLC: $SiO_2$, $R_f$0.25 (10% $MeOH/CH_2Cl_2$).

Step 8: The preparation of Example 48: [1-(3,3-Dimethyl-butyl)-piperidin4-yl]-(3-methyl-but-2-enyl)-(4-phenethyl-phenyl)-amine was prepared in accordance with the methods of Step 8 in Example 37 except that (3-Methyl-but-2-enyl)-(4-phenethyl-phenyl)-piperidin-4-yl-amine (48g) was used instead of [4-(3,3-Dimethyl-butyl)-phenyl]-(3-methyl-but-2-enyl)-pipendin-4-yl-amine (37g) and 3,3-dimethylbutyraldehyde was used instead of isovaleraldehyde.

MS: 428 (M+1 for $C_{30}H_{40}N_2$); an oil; TLC: $SiO_2$, $R_f$0.2 (1:2 hexanes/EtOAc).

Scheme IX

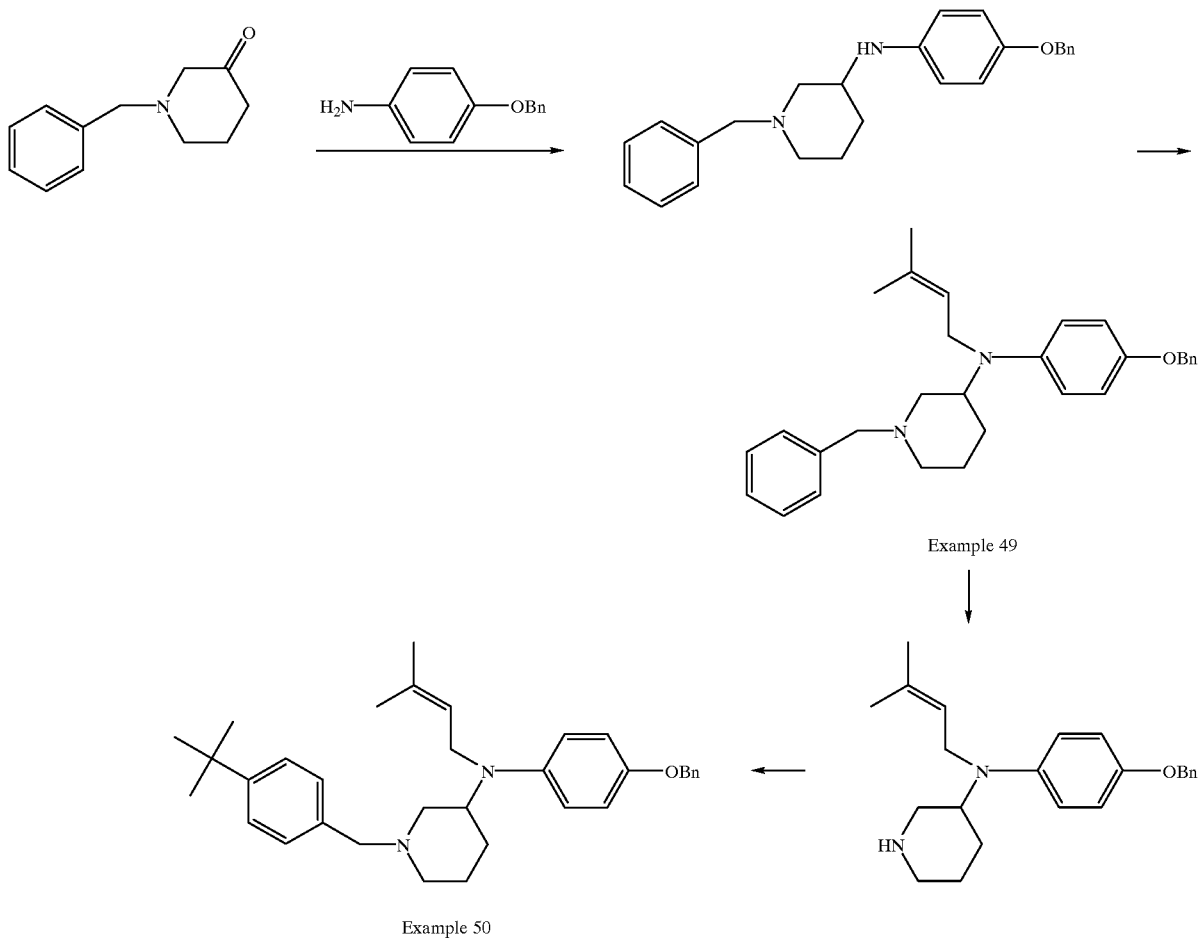

Example 49

(4-Benzyloxy-phenyl)-(1-benzyl-piperidin-3-yl)-(3-methyl-but-2-enyl)-amine

Step 1: (4-Benzyloxy-phenyl)-(1-benzyl-piperidin-3-yl)-amine (49a) was prepared in accordance with the procedures in Example 1 (Step 1) except that 1-benzyl-3-piperidone was used instead of 1-Boc-4-piperidone.

MS: 373 (M+1 for $C_{25}H_{28}N_2O_1$); TLC: $SiO_2$ $R_f$ 0.6 (5% MeOH/$CH_2Cl_2$);

Analysis ($C_{25}H_{28}N_2O_1$): (Cal.) C: 79.84, H: 7.61, N: 7.45, (found) C: 79.83, H: 7.56, N: 7.45.

Step 2: The preparation of Example 49: (4-Benzyloxy-phenyl)-( 1-benzyl-piperidin-3-yl)-(3-methyl-but-2-enyl)-amine was prepared in accordance with the procedure in Example 1 (Step 2) except that (4-Benzyloxy-phenyl)-( 1-benzyl-piperidin-3-yl)-amine (49a) was used instead of 4-(4Benzyloxy-phenylarnino)-piperidine-1-carboxylic acid tert-butyl ester (Ia).

MS: 441 (M+1 for $C_{30}H_{36}N_2O_1$); oil; TLC: $SiO_2$ $R_f$=0.5 (66% hexanes/EtOAc);

Analysis ($C_{30}H_{36}N_2O_1$): (Cal.) C: 81.78, H: 8.24, N: 6.36, (found) C: 81.81, H: 8.26, N: 6.31.

Example 50

(4-Benzyloxy-phenyl)-[1-(4-tert-butyl-benzyl)-piperidin-3-Yl]-(3-methyl-but-2-enyl)-amine Step 1: The preparation of (4-Benzyloxy-phenyl)-(1-piperidin-3-yl)-(3-methyl-but-2-enyl)-amine (50a): (4-Benzyloxy-phenyl)-(1-benzyl-piperidin-3-yl)-(3-methyl-but-2-enyl)-amine (49b) (0.90 g, 2.04 mmol) was dissolved in 1,2-dichloroethane (20 mL), cooled to 0° C., and treated with α-chloroethylchloroformate (0.24 mL, 2.04 mmol). The reaction was stirred cold for 15 minutes, then heated to 60° C. for 1 hour. The reaction was cooled to room temperature, concentrated in vacuo, re-dissolved in MeOH (20 mL), heated to 50° C. for 1 hour, then concentrated in vacuo to give 0.86 g (>100%) of the crude material which was carried on without further purification.

MS: 351 (M+1 for $C_{23}H_{30}N_2O$); oil; TLC: $SiO_2$ $R_f$=0.1 (10% MeOH/$CH_2Cl_2$).

Step 2: The preparation of Example 50: (4-Benzyloxy-phenyl)-[1-(4-tert-butyl-benzyl)-piperidin-3-yl]-(3-methyl-but-2-enyl)-amine was prepared in accordance with methods of Example 3 except that (4-Benzyloxy-phenyl)-(1-piperidin-3-yl)-(3-methyl-but-2-enyl)-amine (50a) was used instead of (4-Benzyloxy-phenyl)-(3-methyl-but-2-enyl)-piperidin-4-yl-amine (Ic).

MS: 497.3 (M+1 for $C_{34}H_{44}N_2O_1$); an oil; TLC: $SiO_2$ $R_f$=0.37 (5% MeOH/$CH_2Cl_2$);

HPLC (C-18 column, 1:1 $CH_3CN/H_2O$+0.5% TFA): RT=15.162 min, 93% pure.

BIOLOGICAL ACTIVITY

The compounds of the present invention exhibit valuable biological properties because of their ability to block calcium flux through N-type voltage-gated calcium channels. To measure interaction at the N-type $Ca^{2+}$ channel and calcium flux inhibition, the effects of the compounds of the present invention were measured in the assays described below.

Measurement of N-type $Ca^{2+}$ Channel Blocking Potencies of Compounds in

IMR-32 Cells Using the Fluorescent $Ca^{2+}$ Indicator Indo-1

IMR-32 cells are a human tumor cell line of neural origin. The IMR-32 cell line has been shown to contain both N- and L-type voltage sensitive calcium channels. Calcium flux into these cells may be induced by stimulation with elevated potassium concentrations. The L-channel component of calcium flux may be blocked by adding 5 µM nitrendipine. The remaining component of calcium entry into the IMR-32 cells is due to calcium flux through N-type calcium channels. Intracellular calcium concentrations are measured, using the fluorescent calcium indicator Indo-1. The effect of drug concentration on calcium uptake is studied.

Methods

The IMR-32 cell line was obtained from the American Type Culture Collection (Rockville, Md.). Cells were grown in Eagle's Minimum Essential Medium with Earle's salts supplemented with 10% fetal bovine serum, 2 mM L-Gln and antibiotic/antimycotic mixture (Gibco). At approximately 80% confluency, differentiation was induced by the addition of 1 mM dibutyryl cAMP and 2.5 µM bromodeoxyuridine to the medium. After seven to thirteen days of differentiation, cells were detached using 0.5 mM EDTA and loaded with five 1M Indo-1 acetoxymethyl ester (Molecular Probes, Eugene, Oreg.) at 30° C. for forty-five minutes. Loaded cells were washed twice, resuspended (~$10^7$ cells/mL) in assay buffer (10 mM HEPES/Tris pH 7.4 in Hank's Balanced Salt Solution without bicarbonate or phenol red containing 0.5% bovine serum albumin) and kept on ice until use. Fluorescence measurements were carried out in a Photon Technology International (PTI, South Brunswick, N.J.) Model RF-F3004 spectrofluorometer with dual emission monochromators using excitation and 350 nm and emission at 400 and 490 nm. The instrument was equipped with a thermostated cuvette holder with stirring capabilities as well as with a computer-controlled pump which allowed for reagent addition during measurement. Instrument control and data collection was done by PTI's OSCAR software running on an IBM compatible computer. Different concentrations of the test compounds (60 µL in dimethyl sulfoxide) were added to 5.94 mL of assay buffer containing approximately $3\times10^6$ loaded cells, and 5 µM Nitrendipine (in 30 µL EtOH) to block L-type $Ca^{2+}$ channels. Samples were incubated for ten minutes at 30° C. and then aliquoted into three 10×10 mm disposable acrylic cuvettes. Emission signals at 400 and 490 nm were acquired from each cuvette at 30° C. for fifty seconds. At twenty seconds after the start of reading, cells were depolarized by the addition of 160 µL of stimulation solution (1M KCl, 68 mM $CaCl_2$) to the cuvette via the computer-controlled pump. Ratio of dual emission signals (400 nm/490 nm), which is proportional to intracellular $Ca^{2+}$ concentration, was plotted against time, and the difference between maximal response after stimulation and basal value (before stimulation) was determined. Values obtained in this way were plotted as a function of drug concentration. $IC_{50}$ values of test compounds were calculated by fitting a four-parameter logistic function to the data using the least squares method.

In Vivo Biological Protocol

A compound of the present invention was dissolved in water using 10% (weight/volume) Emulphor (GAF Corp., Wayne, N.J.) surfactant. Substances were administered by intravenous injection into the retro-orbital venous sinus. All testing was performed fifteen minutes or forty-five minutes after drug injection. All the male mice, 3–4 weeks old were obtained from Jackson Laboratories Bar Harbour, Me. Immediately before anticonvulsant testing, mice were placed upon a wire mesh, four inches square suspended from a steel rod. The square was slowly inserted through 180 degree and mice observed for thirty seconds. Any mouse falling from the wire mesh was scored as ataxia.

Mice were placed into an enclosed acrylic plastic chamber (21 cm height, approximately 30 cm diameter) with a high-frequency speaker (4 cm diameter) in the center of the top lid. An audio signal generator (Protek model B-810) was used to produe a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for one minute. DBA/2 mice in the vehicle-treated group responded to the sound stimulus (applied until tonic extension occurred, or for a maximum of sixty seconds) with a characteristic seizure sequence consisting of wild running followed by clonic seizures and later by tonic extension, and finally by respiratory arrest and death in 80% or more of the mice. In vehicle-treated mice, the entire sequence of seizures to respiratory arrest lasts approximately 15–20 seconds.

The incidence of all the seizure phases in the drug-treated and vehicle-treated mice was recorded, and the occurrence of tonic seizures were used for calculating anticonvulsant $ED_{50}$ values by probit analysis. Mice were used only once for testing at each time and dose point. Results of this assay are shown below in Table 2.

Anti-Writhing Test in Mice (AW) Test Protocol

The purpose of this test is to evaluate drugs for analgesic-like activity. The AW test determines the effect of drugs on the response to a presumed painful stimulus in mice and is used as a preliminary in vivo procedure for the identification of potential analgesic agents.

Known analgesics with low, moderate, or high efficacy in man allow mice to tolerate intra-peritoneal administration of dilute acetic acid as evidenced by lesser incidence of writhing movements. The AW test measures the nociceptive response to acetic acid in mice and provides an objective, reliable, and quantitative estimate of efficacy and potency of potential analgesic compounds. This test serves as a preclinical predictor of analgesic activity.

Subjects are male Swiss-Webster mice (25–35 g).

Compounds are dissolved or suspended in physiological saline containing 2% Emulphor. Suspensions are subjected to ultrasonication for 3 minutes. Drug doses are expressed as the active moiety and are normally administered to mice (10, 30, and 100 mg/kg IP, SC, PO, or IM) in a volume of 10 mL/kg, 1 hour prior to testing; ICV doses (in µg/kg) are administered in a volume of 0.5 mL/kg, 5 minutes prior to testing. Animals dosed PO are fasted for 16 hours prior to dosing. Groups of eight mice are tested with each dose or the vehicle solution (control group).

Mice are treated with a dilute solution of acetic acid (0.6%, 10 mL/kg IP) which elicits writhing. In four successive trials, one pair of mice from each treatment group is placed in one of four adjacent clear plexiglas chambers (4 in×4 in×4 in). This allows the simultaneous observation of four pairs of mice representing all treatments and controls throughout the test. Writhing movements (abdominal contractions, stretching of the torso and hind legs, and concave arching of the back) are counted for 5 minutes commencing 7 minutes after acetic acid administration.

Drug effects on acetic acid-induced writhing are expressed as percent suppression of writhing relative to the vehicle-treated control group run in parallel with treated animals. The writhing tallies from pairs of animals are summed for each treatment and are divided by the summed writhing in the control group. The $ED_{50}s$ for suppression of writhing are determined by nonlinear regression analysis. Each dose is assigned a rating as follows:

N=not active: 0–30% inhibition of writhing
C=moderately active: 31–60% inhibition
A=active: 61–100% inhibition

TABLE 1

In Vitro Results

| Example Number | IMR 32 % of Blockade @ $\mu M$ |
|---|---|
| 1 | 79% @ 10, 40% @ 1 |
| 2 | 93% @ 10, 62% @ 1 |
| 3 | 96% @ 1 |
| 4 | 94% @ 10, 63% @ 1 |
| 5 | 100% @ 10, 47% @ 1 |
| 6 | $IC_{50}$ = 0.33 |
| 7 | $IC_{50}$ = 0.58 |
| 8 | 71% @ 10, 16% @ 1 |
| 9 | 100% @ 10, 30% @ 1 |
| 10 | 62% @ 10, 15% @ 1 |
| 11 | 80% @ 10, 41% @ 1 |
| 12 | 75% @ 10, 49% @ 1 |
| 13 | 75% @ 10, 37% @ 1 |
| 14 | 88% @ 10, 44% @ 1 |
| 15 | 92% @ 10, 51% @ 1 |
| 16 | 78% @ 10, 45% @ 1 |
| 17 | 76% @ 10, 86% @ 1 |
| 18 | $IC_{50}$ = 0.92, 88% @ 10, 60% @ 1 |
| 19 | $IC_{50}$ = 0.72 $\mu M$ |
| 20 | $IC_{50}$ = 3.0 $\mu M$ |
| 21 | $IC_{50}$ = 3.9 $\mu M$ |
| 22 | $IC_{50}$ = 0.50 $\mu M$ |
| 23 | $IC_{50}$ = 0.30 $\mu M$ |
| 24 | $IC_{50}$ = 1.8 $\mu M$ |
| 25 | 62% @ 1 $\mu M$ |
| 26 | 43% @ 1 $\mu M$ |
| 27 | 15% @ 1 $\mu M$ |
| 28 | 41% @ 1 $\mu M$ |
| 29 | 84% @ 10 $\mu M$, 17% @ 1 $\mu M$ |
| 30 | 79% @ 10 $\mu M$, 18% @ 1 $\mu M$ |
| 31 | 62% @ 10 $\mu M$, 7% @ 1 $\mu M$ |
| 32 | 70% @ 10 $\mu M$, 0% @ 1 $\mu M$ |
| 33 | 98% @ 10 $\mu M$, 54% @ 1 $\mu M$ |
| 34 | 76% @ 10 $\mu M$, 23% @ 1 $\mu M$ |
| 35 | 37% @ 1 $\mu M$ |
| 36 | 74% @ 10 $\mu M$, 26% @ 1 $\mu M$ |
| 37 | 92% @ 10 $\mu M$, 31% @ 1 $\mu M$ |
| 38 | 83% @ 10 $\mu M$, 38% @ 1 $\mu M$ |
| 39 | 85% @ 1 $\mu M$, 60% @ 1 $\mu M$ |
| 40 | 72% @ 1 $\mu M$ |
| 41 | $IC_{50}$ = 1.5 $\mu M$ |
| 42 | 81% @ 10 $\mu M$, 60% @ 1 $\mu M$ |
| 43 | 99% @ 10 $\mu M$, 65% @ 1 $\mu M$ |
| 44 | 107% @ 10 $\mu M$, 64% @ 1 $\mu M$ |
| 45 | 85% @ 10 $\mu M$, 28% @ 1 $\mu M$ |
| 46 | 98% @ 10 $\mu M$, 55% @ 1 $\mu M$ |
| 47 | $IC_{50}$ = 0.9 $\mu M$ |
| 49 | $IC_{50}$ = 1.2 $\mu M$ |
| 50 | 96% @ 10 $\mu M$, 86% @ 1 $\mu M$ |

TABLE 2

In Vivo Results

| Example | DBA/2 mice % Protection (dose) | Anti-Writhing % Protection (dose) |
|---|---|---|
| 1 | 100% @ 30 mg/kg | |
| 2 | 80% @ 10 mg/kg | 49% (10 mg/kg) |
| 5 | 80% @ 10 mg/kg | |
| 6 | 100% @ 30 mg/kg | |
|   | 100% @ 10 mg/kg | |
| 7 | 100% @ 30 mg/kg | |
|   | 100% @ 10 mg/kg | |
| 8 | 60% (10 mg/kg) | |
| 15 | 100% @ 30 mg/kg (45 min) | |
|   | 20% @ 10 mg/kg | |
| 19 | 80% (10 mg/kg) | 32% (10 mg/kg) |
| 20 | 40% (10 mg/kg) | |
| 26 | | 11% (10 mg/kg) |
| 39 | | 95% (10 mg/kg) |
| 42 | | 6.5% (10 mg/kg) |
| 44 | 100% (30 mg/kg) | 100% (30 mg/kg) |
|   | | 30% (10 mg/kg) |

What is claimed is:

1. A method of treating pain, the method comprising administering to a patient having pain a therapeutically effective amount of a compound of the formula

I

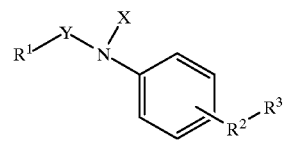

wherein each n is independently 0 to 3;

$R^1$ is $C_1$–$C_8$ alkyl, substituted $C_1$–$C_8$ cycloalkyl, $C_3$–$C_8$ cycloalkyl, substituted $C_3$–$C_8$ cycloalkyl hetercycloalkyl, substituted heterocycloalkyl, $C_2$–$C_8$ alkenyl, $C_3$–$C_8$ cycloalkenyl, aryl, substituted aryl, heteroaryl, substituted hetroaryl, or arylalkyl;

Y is

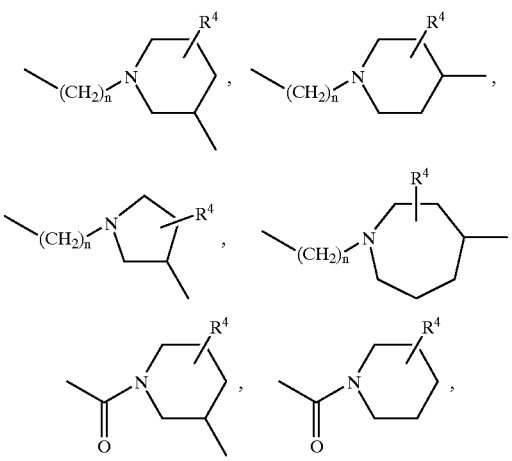

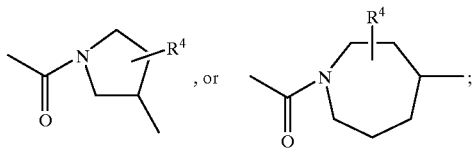

X is 3-methyl-but-2-enyl or 3-methyl-butyl;

R² is absent, —O—, (CH₂)ₙ-, O(CH₂)ₙ-, (CH₂)ₙO—, N(R⁵)(CH₂)ₙ, (CH₂)ₙN(R⁵)-, S(CH₂)ₙ-, (CH₂)ₙS—, —C═C—, or —C≡C—;

R³ is monocyclic aryl, substituted monocyclic aryl, heteroaryl, substituted heteroaryl, heterocyclic, substituted heterocyclic, C₁–C₈ alkyl, substituted C₁–C₈ alkyl C₃–C₁₀ cycloalkyl, substituted C₃–C₁₀ cycloalkyl;

R⁴, R⁵ are independently H or C₁–C₈ alkyl; and the pharmaceutically acceptable salts, esters, amides, and prodrugs thereof.

2. A method of treating pain, the method comprising administering to a patient having pain a therapeutically effective amount of a compound selected from (4-Benzyloxy-phenyl)-(3-methyl-but-2-enyl)-[1-(3-methyl-butyl)-piperidin-4-yl]-amine;

(4-Benzyloxy-phenyl)-[1-(3,3-dimethyl-butyl)-piperidin-4-yl]-(3-methyl-but-2-enyl)-amine;

(4-Benzyloxy-phenyl)-[1-(4-tert-butyl-benzyl)-piperidin-4-yl]-(3-methyl-but-2-enyl)-amine;

(4-Benzyloxy-phenyl)-[1-(4-bromo-benzyl)-piperidin4-yl]-(3-methyl-but-2-enyl)-amine;

4-{4-[(4-Benzyloxy-phenyl)(3-methyl-but-2-enyl)-amino]-piperidin-1-ylmethyl}-phenol;

(4-Benzyloxy-phenyl)-[1-(4-dimethylamino-benzyl)-piperidin-4-yl]-(3-methyl-but-2-enyl)-amine;

(4-Benzyloxy-phenyl)-(3-methyl-but-2-enyl)-[1-(1H-pyrrol-2-ylmethyl)-piperidin-4-yl]-amine;

(4-Benzyloxy-phenyl)-[1-(1H-imidazol-4-ylmethyl)-piperidin-4-yl]-(3-methyl-but-2-enyl)-amine;

(4-Benzyloxy-phenyl)-(3-methyl-but-2-enyl)-(1-pyridin-2-ylmethyl-piperidin-4-yl)-amine;

(4-Benzyloxy-phenyl)-(3-methyl-but-2-enyl)-[1-(tetrahydro-pyran4-yl)-piperidin-4-yl]-amine;

{4-[(4-Benzyloxy-phenyl)-(3-methyl-but-2-enyl)-amino]-piperidin-1-yl}-[1-(3-methyl-butyl)-piperidin-2-yl]-methanone;

{4-[(4-Benzyloxy-phenyl)-(3-methyl-but-2-enyl)-amino]-piperidin-1-yl}-[1-(3-methyl-butyl)-piperidin-3-yl]-methanone;

{4-[(4-Benzyloxy-phenyl)-(3-methyl-but-2-enyl)-amino]-piperidin-1-yl}-[1-(3-methyl-butyl)-piperidin-4-yl]-methanone;

{4-[(4-Benzyloxy-phenyl)-(3-methyl-but-2-enyl)-amino]-piperidin-1-yl}-[4-methyl-1-(3-methyl-butyl)-piperazin-2-yl]-methanone;

{4-[(4-Benzyloxy-phenyl)-(3-methyl-but-2-enyl)-amino]-piperidin-1-yl}-[4-isopropyl-1-(3-methyl-butyl)-piperazin-2-yl]-methanone;

{4-[(4-Benzyloxy-phenyl)-(3-methyl-but-2-enyl)-amino]-piperidin-1-yl}-[6-methyl-1-(3-methyl-butyl)-piperidin-2-yl]-methanone;

{4-[(4-Benzyloxy-phenyl)-(3-methyl-but-2-enyl)-amino]-piperidin-1-yl}-[4-methyl-1-(3-methyl-butyl)-piperidin-2-yl]-methanone;

{4-[(4-Benzyloxy-phenyl)-(3-methyl-but-2-enyl)-amino]-piperidin-1-yl}-[3-methyl-1-(3-methyl-butyl)-piperidin-2-yl]-methanone; or (4-Benzyloxy-phenyl)-[1-(4-dimethylamino-benzyl)-piperidin-3-yl]-(3-methyl-butyl)-amine.

3. A method of treating pain, the method comprising administering to a patient having pain a therapeutically effective amount of a compound selected from (4-Benzyloxy-phenyl)-[1-(4-tert-butyl-benzyl)-piperidin-4-yl]-(3-methyl-butyl)-amine;

4-Benzyloxy-phenyl)-[1-(4-dimethylamino-benzyl)-piperidin-4-yl]-(3-methyl-butyl)-amine;

(4-Benzyloxy-phenyl)-[1-(4-methoxy-benzyl)-piperidin-4-yl]-(3-methyl-butyl)-amine;

(4-Benzyloxy-phenyl)-[1-(4-ethoxy-benzyl)-piperidin-4-yl]-(3-methyl-butyl)-amine;

(4-Benzyloxy-phenyl)-(3-methyl-butyl)-[1-(1H-pyrrol-2-ylmethyl)-piperidin-4-yl]-amine;

(4-Benzyloxy-phenyl)-(3-methyl-butyl)-[1-(4-methylsulfanyl-benzyl)-piperidin4-yl]-amine;

(4-Benzyloxy-phenyl)-[1-(4-methanesulfinyl-benzyl)-piperidin-4-yl]-(3-methyl-butyl)-amine;

(4-Benzyloxy-phenyl)-[1-(4-isopropoxy-benzyl)-piperidin-4-yl]-(3-methyl-butyl)-amine; or (4-Benzyloxy-phenyl)-[1-(4-tert-butyl-benzyl)-piperidin-3-yl]-(3-methyl-butyl)-amine.

4. A method of treating pain, the method comprising administering to a patient having pain a therapeutically effective amount of a compound selected from (4-Benzyloxy-phenyl)-[1-(4-methoxy-benzyl)-piperidin-3-yl]-(3-methyl-butyl)-amine;

(4-Benzyloxy-phenyl)-[1-(4-ethoxy-benzyl)-piperidin-3-yl]-(3-methyl-butyl)-amine;

(4-Benzyloxy-phenyl)-(3-methyl-butyl)-[1-(1H-pyrrol-2-ylmethyl)-piperidin-3-yl]-amine;

(4-Benzyloxy-phenyl)-(3-methyl-butyl)-[1-(4-methylsulfanyl-benzyl)-piperidin-3-yl]-amine;

(4-Benzyloxy-phenyl)-[1-(4-methanesulfinyl-benzyl)-piperidin-3-yl]-(3-methyl-butyl)-amine;

(4-Benzyloxy-phenyl)-[1-(4-isopropoxy-benyl)-piperidin-3-yl]-(3-methyl-butyl)-amine;

(4-Benzyloxy-phenyl)-[-(4-tert-butyl-benzyl)-piperidin-3-yl]-(3-methyl-but-2-enyl)-amine;

(4-Benzyloxy-phenyl)-[1-(4-dimethylamino-benzyl)-piperidin-3-yl]-(3-methyl-but-2-enyl)-amine;

(4-Benzyloxy-phenyl)-[-(4-methoxy-benzyl)-piperidin-3-yl]-(3-methyl-but-2-enyl)-amine; or (4-Benzyloxy-phenyl)-[1-(4-ethoxy-benzyl)-piperidin-3-yl]-(3-methyl-but-2-enyl)-amine.

5. A method of treating pain, the method comprising administering to a patient having pain a therapeutically effective amount of a compound selected from (4-Benzyloxy-phenyl)-(3-methyl-butyl)-[1-(1H-pyrrol-2-ylmethyl)-piperidin-3-yl]-amine;

(4-Benzyloxy-phenyl)-(3-methyl-but-2-enyl)-1-(4-methylsulfanyl-benzyl)-piperidin-3-yl]-amine;

(4-Benzyloxy-phenyl)-[1-(4-methanesulfinyl-benzyl)-piperidin-3-yl]-(3-methyl-but-2-enyl)-amine;

(4-Benzyloxy-phenyl)-[1-(4-isopropoxy-benzyl)-piperidin-3-yl]-(3-methyl-but-2-enyl)-amine;

(4-Benzyloxy-phenyl)-[1-(4-tert-butyl-benzyl)-pyrrolidin-3-yl]-(3-methyl-butyl)-amine;

(4-Benzyloxy-phenyl)-[1-(4-dimethylamino-benzyl)-pyrrolidin-3-yl]-(3-methyl-butyl)-amine;

(4-Benzyloxy-phenyl)-[1-(4-methoxy-benzyl)-pyrrolidin-3-yl]-(3-methyl-butyl)-amine;

(4-Benzyloxy-phenyl)-[1-(4-ethoxy-benzyl)-pyrrolidin-3-yl]-(3-methyl-butyl)-amine;

(4-Benzyloxy-phenyl)-(3-methyl-butyl)-[1-(1H-pyrrol-2-ylmethyl)-pyrrolidin-3-yl]-amine; or (4-Benzyloxy-phenyl)-(3-methyl-butyl)-[1-(4-methylsulfanyl-benzyl)-pyrrolidin-3-yl]-amine.

6. A method of treating pain, the method comprising administering to a patient having pain a therapeutically effective amount of a compound selected from (4-Benzyloxy-phenyl)-[1-(4-methanesulfinyl-benzyl)-pyrrolidin-3-yl]-(3-methyl-butyl)-amine;

(4-Benzyloxy-phenyl)-[1-(4-isopropoxy-benzyl)-pyrrolidin-3-yl]-(3-methyl-butyl)-amine;

(1-Benzo[1,3]dioxol-5-ylmethyl-piperidin-4-yl)-(4-benzyloxy-phenyl)-(3-methyl-butyl)-amine;

(4-Benzyloxy-phenyl)-[1-(4-bromo-benzyl)-piperidin-4-yl]-(3-methyl-butyl)-amine;

(4-Benzyloxy-phenyl)-[1-(4-chloro-benzyl)-piperidin-4-yl]-(3-methyl-butyl)-amine;

(1-Benzo[1,3]dioxol-5-ylmethyl-piperidin-3-yl)-(4-benzyloxy-phenyl)-(3-methyl-butyl)-amine;

(4-Benzyloxy-phenyl)-[1-(4-bromo-benzyl)-piperidin-3-yl]-(3-methyl-butyl)-amine;

(4-Benzyloxy-phenyl)-[1-(4-chloro-benzyl)-piperidin-3-yl]-(3-methyl-butyl)-amine;

(1-Benzo[1,3]dioxol-5-ylmethyl-piperidin-3-yl)-(4-benzyloxy-phenyl)-(3-methyl-but-2-enyl)-amine; or (4-Benzyloxy-phenyl)-[1-(4-bromo-benzyl)-piperidin-3-yl]-(3-methyl-but-2-enyl)-amine.

7. A method of treating pain, the method comprising administernng to a patient having pain a therapeutically effective amount of a compound selected from (4-Benzyloxy-phenyl)-[1-(-chloro-benzyl)-piperidin-3-yl]-(3-methyl-but-2-enyl)-amine, (1-Benzo[1,3]dioxol-5-ylmethyl-pyrrolidin-3-yl)-(4-benzyloxy-phenyl)-(3-methyl-but-2-enyl)-amine;

(4-Benzyloxy-phenyl)-[1-(4-bromo-benzyl)-pyrrolidin-3-yl]-(3-methyl-but-2-enyl)-amine;

(4-Benzyloxy--phenyl)-[1-(4-chloro-benzyl)pyrrolidin-3-yl]-(3-methyl-but-2-enyl)-amine;

N-Benzyl-N'-[1-(4-tert-butyl-benzyl)-piperidin-4-yl]-N'-(3-methyl-but-2-enyl)-benzene-1,4-diamine;

N-Benzyl-N'-[1-(4-dimethylamino-benzyl)-piperidin-4-yl]-N'-(3-methyl-but-2-enyl)-benzene-1,4-diamine;

N-Benzyl-N'-{[1-(3,3-dimethyl-butyl)]-piperidin-4-yl}-N'-(3-methyl-but-2-enyl)-benzene-1,4-diamine;

N-Benzyl-N'-[1-(4-bromo-benzyl)-piperidin-4-yl]-N'-(3-methyl-but-2-enyl)-benzene-1,4-diamine;

N-Benzyl-N'-[1-(4-methoxy-benzyl)-piperidin-4-yl]-N'-(3-methyl-but-2-enyl)-benzene-1,4-diamine; or

[1-(4-Dimethylamino-benzyl)-piperidin-4-yl]-(3-methyl-but-2-enyl)-(4-phenethyl-phenyl)-amine.

8. A method of treating pain, the method comprising administering to a patient having pain a therapeutically effective amount of a compound selected from (1-Benzo[1,3]dioxol-5-ylmethyl-piperidin-4-yl)-(4-benzyloxy-phenyl)-(3-methyl-but-2-enyl)-amine;

(4-Benzyloxy-phenyl)-[1-(4-methanesulfinyl-benzyl)-piperidin-4-yl]-(3-methyl-but-2-enyl)-amine;

(4-Benzyloxy-phenyl)-[1-(4-isopropoxy-benzyl)-piperidin4-yl]-(3-methyl-but-2-enyl)-amine;

(4-Benzyloxy-phenyl)-(3-methyl-but-2-enyl)-[1-(4-methylsulfanyl-benzyl)-piperidin-4-yl]-amine;

(4-Benzyloxy-phenyl)-[1-(4-ethoxy-benzyl)-piperidin-4-yl]-(3-methyl-but-2-enyl)-amine;

(4-Benzyloxy-phenyl)-[1-(3-methoxy-3-methyl-butyl)-piperidin4-yl]-(3-methyl-but-2-enyl)-amine;

(4-Benzyloxy-phenyl)-(3-methyl-but-2-enyl)-(1-pentyl-piperidin-4-yl)-amine;

(4-Benzyloxy-phenyl)-[1-(3,3-dimethyl-butyl)-piperidin-4-yl]-(3-methyl-butyl)-amine;

(4-Benzyloxy-phenyl)-[1-(3-methoxy-3-methyl-butyl)-piperidin-4-yl]-(3-methyl-butyl)-amine; or (4-Benzyloxy-phenyl)-(3-methyl-butyl)-(1-pentyl-piperidin-4-yl)-amine.

9. A method of treating pain, the method comprising administering to a patient having pain a therapeutically effective amount of a compound selected from {4-[(4-Benzyloxy-phenyl)-(3-methyl-butyl)-amino]-piperidin-1-yl}-[4-methyl-1-(3-methyl-butyl)-piperazin-2-yl]-methanone;

{4-[(4-Benzyloxy-phenyl)-(3-methyl-butyl)-amino]-piperidin-1-yl}-[4-isopropyl-1-(3-methyl-butyl)-piperazin-2-yl]-methanone;

{4-[(4-Benzyloxy-phenyl)-(3-methyl-butyl)-amino]-piperidin-1-yl}-[4-methyl-1-(3-methyl-butyl)-piperidin-2-yl]-methanone;

(4-Benzyloxy-phenyl)-[1-(3,3-dimethyl-butyl)-piperidin-3-yl]-(3-methyl-butyl)-amine;

(4-Benzyloxy-phenyl)-[1-(3-methoxy-3-methyl-butyl)-piperidin-3-yl]-(3-methyl-butyl)-amine;

(4-Benzyloxy-phenyl)-(3-methyl-butyl)-(1-pentyl-piperidin-3-yl)-amine;

{3-[(4-Benzyloxy-phenyl)-(3-methyl-butyl)-amino]-piperidin-1-yl}-[4-methyl-1-(3-methyl-butyl)-piperazin-2-yl]-methanone;

{3-[(4-Benzyloxy-phenyl)-(3-methyl-butyl)-amino]-piperidin-1-yl}-[4-isopropyl-1-(3-methyl-butyl)-piperazin-2-yl]-methanone;

{3-[(4-Benzyloxy-phenyl)-(3-methyl-butyl)-amino]-piperidin-1-yl}-[4-methyl-1-(3-methyl-butyl)-piperidin-2-yl]-methanone; or (4-Benzyloxy-phenyl)-[1-(3,3-dimethyl-butyl)-piperidin-3-yl]-(3-methyl-but-2-enyl)-amine.

10. A method of treating pain, the method comprising administering to a patient having pain a therapeutically effective amount of a compound selected from (4-Benzyloxy-phenyl)-[1-(3-methoxy-3-methyl-butyl)-piperidin-3-yl]-(3-methyl-but-2-enyl)-amine;

(4-Benyloxy-phenyl)-(3-methyl-but-2-enyl)-(1-pentyl-piperidin-3-yl)-amine;

{3-[(4-Benzyloxy-phenyl)-(3-methyl-but-2-enyl)-amino]-piperidin-1-yl}-[4-methyl-1-(3-methyl-butyl)-piperazin-2-yl]-methanone;

{3-[(4-Benzyloxy-phenyl)-(3-methyl-but-2-enyl)-amino]-piperidin-1-yl}- [4-isopropyl-1-(3 -methyl-butyl)-piperazin-2-yl]-methanone;

{3-[(4-Benzyloxy-phenyl)-(3-methyl-but-2-enyl)-amino]-piperidin-1-yl}-[4-methyl-1-(3-methyl-butyl)-piperidin-2-yl]-methanone;

(4-Benzyloxy-phenyl)-[1-(3,3-dimethyl-butyl)-pyrrolidin-3-yl]-(3-methyl-but-2-enyl)-amine;

(4-Benzyloxy-phenyl)-[1-(3-methoxy-3-methyl-butyl)-pyrrolidin-3-yl]-(3-methyl-but-2-enyl)-amine;

(4-Benzyloxy-phenyl)-(3-methyl-but-2-enyl)-(1-pentyl-pyrrolidin-3-yl)-amine;

{3-[(4-Benzyloxy-phenyl)-(3-methyl-but-2-enyl)-amino]-pyrrolidin-1-yl}-[4-methyl-1-(3-methyl-butyl)-piperazin-2-yl]-methanone;

{3-[(4-Benzyloxy-phenyl)-(3-methyl-but-2-enyl)-amino]-pyrrolidin-1-yl}-[4-isopropyl-1-(3-methyl-butyl)-piperazin-2-yl]-methanone; or {3-[(4-Benzyloxy-phenyl)-(3-methyl-but-2-enyl)-amino]-pyrrolidin-1-yl}-[4-methyl-1-(3-methyl-butyl)-piperidin-2-yl]-methanone.

11. A method of treating pain, the method comprising administering to a patient having pain a therapeutically effective amount of a compound selected from (4-Benzyloxy-phenyl)-(1-benzyl-piperidin-4-yl)(3-methyl-but-2-enyl)-amine;

4-{4-[(4-Benzyloxy-phenyl)-(3-methyl-but-2-enyl)-amino]-piperidin-1-yl}-butan-2-ol;

(4-Benzyloxy-phenyl)-(1-furan-2-ylmethyl-piperidin-4-yl)-(3-methyl-but-2-enyl)-amine;

(4-Benzyloxy-phenyl)-(3-methyl-but-2-enyl)-[1-(3-phenyl-propyl)-piperidin-4-yl]-amine;

(4-Benzyloxy-phenyl)-(3-methyl-but-2-enyl)-(1-phenethyl-piperidin-4-yl)-amine;

(4-Benzyloxy-phenyl)-[1-(4-methanesulfonyl-benzyl)-piperidin-4-yl]-(3-methyl-but-2-enyl)-amine;

(4-Benzyloxy-phenyl)-[1-(4-fluoro-benzyl)-piperidin-4-yl]-(3-methyl-but-2-enyl)-amine;

[1-(3,3-Dethyl-butyl)-piperidin4-yl]-(4-isopropyl-phenyl)-(3-methyl-but-2-enyl)-amine;

4-{4-[(4-Isopropyl-phenyl)-(3-methyl-but-2-enyl)-amino]-piperidin-1-yl}- butan-2-ol; or (4-Isopropyl-phenyl)-(3-methyl-but-2-enyl)-[1-(3-methyl-butyl)-piperidin-4-yl]-amine.

12. A method of treating pain, the method comprising administering to a patient having pain a therapeutically effective amount of a compound selected from

[1-(4-Fluoro-benzyl)-piperidin-4-yl]-(4-isopropyl-phenyl)-(3-methyl-but-2-enyl)-amine;

(4-Isopropyl-phenyl)-(3-methyl-but-2-enyl)-(1-pyridin-3-ylmethyl-piperidin-4-yl)-amine;

[1-(1H-Imidazol-4-ylmethyl)-piperidin-4-yl]-(4-isopropyl-phenyl)-(3-methyl-but-2-enyl)-amine;

2-{4-[(4-Isopropyl-phenyl)-(3-methyl-but-2-enyl)-amino]-piperidin-1-yl}-propan-1-ol;

(4-Isopropyl-phenyl)-(3-methyl-but-2-enyl)-[1-(1H-pyrrol-2-ylmethyl)-piperidin4-yl]-amine;

(4-Isopropoxy-phenyl)-(3-methyl-but-2-enyl)-[-(3-methyl-butyl)-piperidin-4-yl]-amine;

[1-(4-Fluoro-benzyl)-piperidin4-yl]-(4-isopropoxy-phenyl)-(3-methyl-but-2-enyl)-amine;

1-(3,3-Dimethyl-butyl)-piperidin-4-yl]-(4-isopropoxy-phenyl)-(3-methyl-but-2-enyl)amine;

[4-(3,3-Dimethyl-butyl)-phenyl]-(3-methyl-but-2-enyl)-[1-(3-methyl-butyl)-piperidin-4-yl]-amine; or 4-(3,3-Dimethyl-butyl)-phenyl]-[1-(3,3-dimethyl-butyl)-piperidin-4-yl]-(3-methyl-but-2-enyl)-amine.

13. A method of treating pain, the method comprising administering to a patient having pain a therapeutically effective amount of a compound selected from

[1-(4-Dimethylamino-benzyl)-piperidin-4-yl]-[4-(3,3-dimethyl-butyl)-phenyl]-(3-methyl-but-2-enyl)-amine;

(4-Cyclohexylmethoxy-phenyl)-(3-methyl-butyl)-[1-(3-methyl-butyl)-piperidin-4-yl]-amine;

4-{4-[(4-Cyclohexylmethoxy-phenyl)-(3-methyl-butyl)-amino]-piperidin-1-yl}-butan-2-ol;

(4-Cyclohexylmethoxy-phenyl)-[1-(3,3-dimethyl-butyl)-piperidin-4-yl]-(3-methyl-butyl)-amine;

[1-(3,3 -Dimethyl-butyl)-piperidin-4-yl]-[4-(4-fluoro-benzyloxy)-phenyl]-(3-methyl-butyl)-amine;

(S)-1-{4-[(4-Benzyloxy-phenyl)-(3-methyl-but-2-enyl)-amino]-piperidin-1-yl}-2-hydroxy-4-methyl-pentan-1-one;

(S)-2-Hydroxy-1-{4-[(4-isopropyl-phenyl)-(3-methyl-but-2-enyl)-amino]-piperidin-1-yl}4-methyl-pentan-1-one;

(3-Benzyloxy-phenyl)[1-(3,3-dimethyl-butyl)-piperidin-4-yl]-(3-methyl-but-2-enyl)-amine;

[4-(3,3-Dimethyl-butyl)-phenyl]-(3-methyl-but-2-enyl)-[1-(1H-pyrrol-2-ylmethyl)-piperidin-4-yl]-amine; or

[1-(3,3-Dimethyl-butyl)-piperidin-4-yl]-(3-methyl-but-2-enyl)-(4-phenethyl-phenyl)-amine.

14. A method of treating pain, the method comprising administering to a patient having pain a therapeutically effective amount of a compound selected from (4-Benzyloxy-phenyl)-[1-(4-tert-butyl-benzyl)-piperidin-3-yl]-(3-methyl-but-2-enyl)-amine;

(4-Benzyloxyphenyl)-[1-(4-tert-butyl-benzyl)-piperidin-3-yl]-(3-methyl-but-2-enyl)-amine;

(1-Cyclohexylmethyl-piperidin-4-yl(4-isopropyl-phenyl)-(3-methyl-but-2-enyl)-amine;

(4-Isopropyl-phenyl)-(3-methyl-but-2-enyl)-[1-(tetrahydro-pyran-4-yl)-piperidin-4-yl]-amine;

(1-Cyclohexyl-piperidin4-yl)-(4-isopropyl-phenyl)-(3-methyl-but-2-enyl)-amine;

[4-(4-Fluoro-benzyloxy)-phenyl]-(3-methyl-butyl)-[1-(3,3,3-trifluoro-propyl)-piperidin-4-yl]-amine;

(4-Cyclohexylmethoxy-phenyl)-(3-methyl-butyl)-[1-(3,3,3-trifluoro-propyl)-piperidin-4-yl]-amine;

(1-Furan-3-ylmethyl-piperidin-4-yl)-(4-isopropyl-phenyl)-(3-methyl-but-2-enyl)-amine;

(4-Isopropyl-phenyl)-(3-methyl-but-2-enyl)-(1-thiophen-3-ylmethyl-piperidin-4-yl)-amine; or

[1-(3,3-Dimethyl-butyl)-piperidin-4-yl]-[4-(furan-3-ylmethoxy)-phenyl]-(3-methyl-butyl)-amine.

15. A method of treating pain, the method comprising administering to a patient having pain a therapeutically effective amount of a compound selected from

[1-(4-Fluoro-benzyl)-piperidin-4-yl]-[4-(furan-3-ylmethoxy)-phenyl]-(3-methyl-butyl)-amine;

[4-(Furan-3-ylmethoxy)-phenyl]-(3-methyl-butyl)-[1-(1H-pyrrol-2-ylmethyl)-piperidin-4-yl]-amine;

[1-(4-Dimethylamino-benzyl)-piperidin4-yl]-(4-isopropyl-phenyl)-(3-methyl-but-2-enyl)-amine;

[4-(4-Fluoro-benzyloxy)-phenyl]-[1-(4-fluoro-benzyl)-piperidin4-yl]-(3-methyl-butyl)-amine;

(4-Benzyloxy-phenyl)-(3-methyl-but-2-enyl)-(1-phenyl-piperidin4-yl)-amine;

(4-Benzyloxy-phenyl)-[1-(4-fluoro-phenyl)-piperidin-4-yl]-(3-methyl-but-2-enyl)-amine;

(4-Benzyloxy-phenyl)-(3-methyl-but-2-enyl)-[1-(4-trifluoromethyl-phenyl)-piperidin-4-yl]-amine;

[4-(4-Fluoro-benzyloxy)-phenyl]-(3-methyl-butyl)-(1-pyridin-2-ylmethyl-piperidin-4-yl)-amine;

[4-(4-Fluoro-benzyloxy)-phenyl]-(3-methyl-butyl)-(1-pyridin-4-ylmethyl-piperidin-4-yl)-amine; or 4-{4-[(4-Isopropyl-phenyl)-(3-methyl-but-2-enyl)-amino]-piperidin-1-ylmethyl}-phenol.

16. A method of treating pain, the method comprising administering to a patient having pain a therapeutically effective amount of a compound selected from (4-Isopropyl-phenyl)-(3-methyl-but-2-enyl)-[1-(3,3,3-trifluoro-propyl)-piperidin-4-yl]-amine;

(4-Cyclohexylmethoxy-phenyl)-(3-methyl-butyl)-[1-(1H-pyrrol-3-ylmethyl)-piperidin-4-yl]-amine;

[4-(4-Fluoro-benzyloxy)-phenyl]-(3-methyl-butyl)-[1-(1H-pyrrol-3-ylmethyl)-piperidin-4-yl]-amine;

(trans)-2-{4-[(4-Benzyloxy-phenyl)-(3-methyl-but-2-enyl)-amino]-piperidin-1-yl}-cyclohexanol;

(4-Benzyloxy-phenyl)-(1-benzyl-piperidin-4-yl)-(3-methyl-butyl)-amine;

(4-Benzyloxy-phenyl-(1-benzyl-piperidin4-yl)-cyclohexylmethyl-amine;

(4-Benzyloxy-phenyl)-(1-benzyl-piperidin-4-yl)-ethyl-amine;

Benzyl-(4-benzyoxy-phenyl)-(1-benzyl-piperidin-4-yl)-amine;

(4-Benzyloxy-phenyl)-[1-(4-dimethylamino-benzyl)-piperidin-3-yl]-(3-methyl-butyl)-amine; or (4-Benzyloxy-phenyl)-(3-methyl-but-2-enyl)-[1-(1H-pyrrol-3-ylmethyl)-piperidin-3-yl]-amine.

17. A method of treating pain, the method comprising administering to a patient having pain a therapeutically effective amount of a compound selected from (1-Benyl-piperidin4-yl)-(3-methyl-butyl)-[4-(pyridin-3-ylmethoxy)-phenyl]-amine;

(4-Benzyloxy-phenyl)-(3-methyl-but-2-enyl)-[1-(3,3,3-trifluoro-propyl)-piperidin4-yl]-amine; or (4-Benzyloxy-phenyl)-[1-(3,3-dimethyl-butyl)-piperidin4-yl]-(3-methyl-butyl)-amine.

* * * * *